United States Patent [19]

Plummer

[11] Patent Number: 4,536,591

[45] Date of Patent: * Aug. 20, 1985

[54] INSECTICIDAL [1,1'-BIPHENYL]-3-YLMETHYL ESTERS

[75] Inventor: Ernest L. Plummer, Yardley, Pa.

[73] Assignee: FMC Corporation, Philadelphia, Pa.

[*] Notice: The portion of the term of this patent subsequent to Jul. 22, 1997 has been disclaimed.

[21] Appl. No.: 464,242

[22] Filed: Feb. 7, 1983

Related U.S. Application Data

[60] Continuation of Ser. No. 265,940, May 21, 1981, Pat. No. 4,402,973, which is a continuation-in-part of Ser. No. 193,056, Oct. 2, 1980, Pat. No. 4,329,518, which is a continuation-in-part of Ser. No. 76,636, Sep. 18, 1979, abandoned, which is a division of Ser. No. 966,405, Dec. 4, 1978, Pat. No. 4,214,004.

[51] Int. Cl.$^3$ ............... C07C 69/743; C07C 69/747; A01N 53/00

[52] U.S. Cl. .................... 560/8; 560/43; 560/59; 560/105; 560/118; 560/124

[58] Field of Search ............ 560/43, 59, 105, 118, 560/124, 8; 424/305, 306, 308, 309

[56] References Cited

U.S. PATENT DOCUMENTS

| | | | |
|---|---|---|---|
| 4,130,657 | 12/1978 | Plummer | 560/124 |
| 4,214,004 | 7/1980 | Plummer | 560/124 |
| 4,238,505 | 12/1980 | Engel | 560/124 |
| 4,402,973 | 9/1983 | Plummer | 560/124 |

OTHER PUBLICATIONS

Elliott, Chem. Soc. Rev. 7, pp. 473-501, (1978).

Primary Examiner—Michael L. Shippen
Attorney, Agent, or Firm—R. L. Hansen; H. R. Ertelt

[57] ABSTRACT

[1,1'-Biphenyl]-3-ylmethyl pyrethroid esters, as well as processes, uses, and intermediates thereto, are disclosed. The [1,1'-biphenyl]-3-ylmethyl pyrethroid esters control a broad spectrum of insects as well as acarids.

3 Claims, No Drawings

INSECTICIDAL [1,1'-BIPHENYL]-3-YLMETHYL ESTERS

This application is a continuation of application Ser. No. 265,940, filed May 21, 1981, U.S. Pat. No. 4,402,973, which is a continuation-in-part of application Ser. No. 193,056, filed Oct. 2, 1980, U.S. Pat. No. 4,329,518, which is a continuation-in-part of application Ser. No. 076,636, filed Sept. 18, 1979, abandoned, which is a division of application Ser. No. 966,405, filed Dec. 4, 1978, now U.S. Pat. No. 4,214,004.

This invention pertains to the field of bioaffecting compositions; more specifically, it pertains to novel carboxylic acid esters which are pyrethroid insecticides, processes and intermediates thereto, insecticidal and acaricidal compositions containing the novel esters, and to the use of the compositions for controlling insects and acarids.

Pyrethrins have long been of interest as insecticides. Ever since it was discovered that pyrethrins are organic esters, various synthetic modifications have been made in the carboxylic acid and in the alcohol moieties on either side of the ester linkage. Many of the synthetic pyrethroids are more effective than the natural pyrethrins, and recent modifications have overcome a chronic pyrethrin problem—instability to air and light.

The carboxylic acid moiety in the aforesaid esters is often a 2,2-dimethylcyclopropane-1-carboxylic acid with various substituents in the 3-position. Many variations in the alcohol moiety of the aforesaid esters have been disclosed also. The alcohols appearing in the most active pyrethroids of current commercial interest are well-known in the prior art and are described by the structural formula

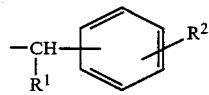

wherein $R^1$ is a hydrogen atom, an alkynyl group, a methyl group, or a cyano group; and $R^2$ is a phenoxy group, a benzyl group, or a phenylthio group. Representative alcohols are 3-phenoxybenzyl alcohol and α-cyano-3-phenoxybenzyl alcohol.

According to M. Elliott, Bull. Wld. Hlth. Org., 44, 315 (1970), it is "essential for powerful pyrethrin-like activity" that the alcohol moiety, represented by HO—[C—D—E—F], contain certain structural units. It is necessary that the unit C be a tetrahedral carbon atom chemically bonded, not only to the alcoholic oxygen atom O, but to unit D, the remainder of a cyclopentenolone ring, a benzene or furan ring, or C=C, so that "the carbon atoms in C, D, and E are coplanar". "The unit E is —CH$_2$—, —O—, or —CO—, or a sterically equivalent link, such that an unsaturated centre F (an olefinic or acetylenic bond, a conjugated system of double bonds, or an aromatic ring) can adopt a position skew to the direction defined by C, D, and E." The alcohol moieties in the most active of the pyrethroid esters of current commercial interest all contain a linking unit E, for example, —O— in the representative alcohols named above. U.S. Pat. No. 4,130,657 discloses that the linking unit E is not required, and [1,1'-biphenyl]-3-ylmethyl 3-(2,2-dihaloethenyl)-2,2-dimethylcyclopropanecarboxylates, wherein the halogen is chlorine or bromine, exhibit insecticidal and acaricidal activity.

Furthermore, U.S. Pat. No. 4,214,004 discloses that [1,1'-biphenyl]-3-ylmethyl 3-(2,2-dihaloethenyl)-2,2-dimethylcyclopropanecarboxylates having substituent groups selected from halo, haloalkyl, lower alkyl, lower alkoxy, and nitro on the benzene rings of the biphenyl unit also exhibit pronounced insecticidal and acaricidal activity, activity which is especially long-lived.

It has now been found that insecticidal and acaricidal esters result when a [1,1'-biphenyl]-3-ylmethyl alcohol moiety is coupled with certain other pyrethroid carboxylic acid moieties.

Like the 3-phenoxybenzyl esters, several of the new pyrethroids are capable of both geometrical and optical isomerism, the biological activity varying somewhat according to the specific isomer. The pure cis geometrical isomer of a [1,1'-biphenyl]-3-ylmethyl pyrethroid ester is usually a more active insecticide and acaricide than the pure trans isomer, and the activity of a [1,1'-biphenyl]-3-ylmethyl pyrethoid ester is a function of the cis/trans ratio.

Although, for the most part, the preparation and testing of racemic esters is described specifically below, the pure optical isomers also display biological activity in varying degrees. The terms "[1,1'-biphenyl]-3-ylmethyl pyrethoid ester" or "substituted [1,1'-biphenyl]-3-ylmethyl cyclopropanecarboxylate" employed herein are intended to include generically all optical and geometrical isomers of the named compounds and mixtures thereof. The term "lower" modifying alkyl or alkoxy means a linear or branched chain of 1–6, preferably 1–4, carbon atoms. The term "halo" employed alone or modifying alkyl means fluorine, chlorine or bromine.

Insecticidal and acaricidal [1,1'-biphenyl]-3-ylmethyl pyrethroid esters of this invention are represented by Formula I

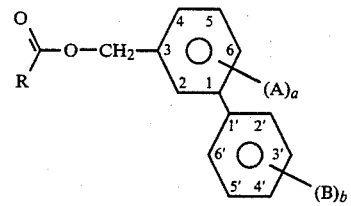

wherein R is an organic radical selected from

Group I consisting of 3-(2,2-dichloroethenyl)-2,2-dimethylcyclopropyl and 3-(2,2-dibromoethenyl)-2,2-dimethylcyclopropyl; or Group II consisting of 2,2,3,3-tetramethylcyclopropyl, 2,2-dichloro-3,3-dimethylcyclopropyl, 3-cyclopentylidenemethyl-2,2-dimethylcyclopropyl, 3-(2-methyl-1-propenyl)-2,2-dimethylcyclopropyl, and 3-(1,2-dibromo-2,2-dichloroethyl)-2,2-dimethylcyclopropyl; or Group III consisting of 3-[(2-chloro-2-phenyl)ethenyl]-2,2-dimethylcyclopropyl, 1-(4-chlorophenyl)-2-methylpropyl, 2,2-dichloro-1-(4-ethoxyphenyl)cyclopropyl, and 1-(2-chloro-4-trifluoromethylphenylamino)-2-methylpropyl; or Group IV consisting of 3-(2-chloro-3,3,3-trifluoro-1-propenyl)-2,2-dimethylcyclopropyl and 3-(3-chloro-2,3,3-trifluoro-1-propenyl)-2,2-dimethylcyclopropyl; and wherein a and b are 0; or b is 0, a is 1–4, and A is halo, haloalkyl, or lower alkyl; or a is 0, b is 1–5, and B is halo, haloalkyl, lower alkyl, or lower alkoxy; or a is 1–4, b is 1–4, and A and B are halo or lower alkyl.

Among the insecticidal and acaricidal [1,1'-biphenyl]-3-ylmethyl pyrethroid esters of Formula I wherein a and b are 0 are those disclosed in U.S. Pat. No. 4,130,657. Other active esters of this type are ([1,1'-biphenyl]-3-yl)methyl 2,2,3,3-tetramethylcyclopropanecarboxylate, ([1,1'-biphenyl]-3-yl)methyl 2,2-dichloro-3,3-dimethylcyclopropanecarboxylate, ([1,1'-biphenyl]-3-yl)methyl 3-cyclopentylidenemethyl-2,2-dimethylcyclopropanecarboxylate, ([1,1'-biphenyl]-3-yl)methyl 3-(2-methyl-1-propenyl)-2,2-dimethylcyclopropanecarboxylate, ([1,1'-biphenyl]-3-yl)methyl 3-(2-chloro-2-phenylethenyl)-2,2-dimethylcyclopropanecarboxylate, ([1,1'-biphenyl]-3-yl)methyl 4-chloro-α-(1-methylethyl)benzeneacetate, and ([1,1'-biphenyl]-3-yl)methyl 2,2-dichloro-1-(4-ethoxyphenyl)cyclopropanecarboxylate, compounds of Formula I wherein R is selected from Group II or Group III.

Noteworthy insecticidal and acaricidal [1,1'-biphenyl]-3-ylmethyl pyrethroid esters are substituted [1,1'-biphenyl]-3-ylmethyl cyclopropanecarboxylates of Formula I wherein a and b are not both zero. In active esters of this type, (1) b is 0, a is 1–4, R is selected from Group I, and when a is 1, A is 2-, 4-, or 6-halo, 5-fluoro, 2-lower alkyl, or 2-trifluoromethyl, and when a is 2, A is fluoro, 2- and 4-substituents independently selected from fluoro, chloro, bromo, and lower alkyl, with the proviso that only one may be bromo or alkyl other than methyl, or 2- and 6-substituents independently selected from fluoro, chloro and methyl, and when a is 3 or 4, A is fluoro, or may be as when a is 1 or a is 2 with one or two additional fluoro groups; or R is selected from Group II, and when a is 1, A is fluoro, 2-chloro, 2-bromo, 2-methyl, or 2-ethyl, and when a is 2, A is fluoro, or 2- and 4-substituents independently selected from fluoro, chloro and methyl, and when a is 3 or 4, A is fluoro, or may be as when a is 1 or a is 2 with one or two additional fluoro groups;

or R is selected from Group III, a is 2 to 4, and A is fluoro; or R is selected from Group IV, a is 3 or 4, and A is fluoro; or (2) a is 0, b is 1–5, R is selected from Group I, and when b is 1, B is halo, 2'- or 3'-lower alkyl, 2' or 3'-trifluoromethyl, or 2'- or 3'-lower alkoxy, and when b is 2, B is fluoro, or 2'- and 4'-substituents independently selected from fluoro, chloro and bromo, and when b is 3, 4 or 5, B is fluoro; or (3) a is 1–4, b is 1–4, R is selected from Group I, and A is fluoro or a 2-substituent selected from chloro, bromo, and lower alkyl with 0 to 3 fluoro groups, and B is fluoro or a 2'-substituent selected from chloro and methyl with 0 to 3 fluoro groups.

Most noteworthy among the just described group of compounds are those in which halo is restricted to fluoro and chloro, and lower alkyl is restricted to methyl, especially wherein a is not greater than 3 and b is not greater than 2.

In general, in the esters wherein a or b, but not both, is 0 and R is selected from Group I, the most desirable Group, the dichloroethenyl compounds are preferred, since the dichloroethenyl compounds are less expensive to prepare. Of the lower alkyl and lower alkoxy substituents, methyl and ethyl and methoxy and ethoxy are preferred. Those compounds wherein a is 0 are desirable, especially those containing a single substituent, B, at the 2'-position. The most preferred compounds of this type are (2'-fluoro-[1,1'-biphenyl]-3-yl)methyl 3-(2,2-dichloroethenyl)-2,2-dimethylcyclopropanecarboxylate and (2'-methyl-[1,1'-biphenyl]-3-yl)methyl 3-(2,2-dichloroethenyl)-2,2-dimethylcyclopropanecarboxylate. When more than one substituent, B, is present, they are preferably halo, especially fluoro.

Among those compounds wherein b is 0 and R is selected from Group I, (2-methyl[1,1'-biphenyl]-3-yl)methyl 3-(2,2-dichloroethenyl)-2,2-dimethylcyclopropanecarboxylate is very active, and among the halo-substituted compounds it is preferred that A be fluoro or chloro, especially fluoro. When the compound has 2-halo substitution, it is preferred that it also be substituted at the 4-position. Among these latter compounds, the cis-isomers are especially active, and so preferred. Most preferred of the cis-isomers are (2,4-dichloro[1,1'-biphenyl]-3-yl)methyl cis-3-(2,2-dichloroethenyl)-2,2-dimethylcyclopropanecarboxylate and (2,4-difluoro-[1,1'-biphenyl]-3-yl)methyl cis-3-(2,2-dichloroethenyl)-2,2-dimethylcyclopropanecarboxylate.

Among those compounds wherein b is 0 and R is selected from Group II, the (2-methyl-[1,1'-biphenyl]-3-yl)methyl, (2,4-dimethyl-[1,1'-biphenyl]-3-yl)methyl, and (2,4,5,6-tetrafluoro-[1,1'-biphenyl]-3-yl)methyl esters are preferred. The most preferred substituted [1,1'-biphenyl]-3-ylmethyl cyclopropanecarboxylates of this type are (2,4-dimethyl-[1,1'-biphenyl]-3-yl)methyl 2,2,3,3-tetramethylcyclopropanecarboxylate, (2,4-dimethyl-[1,1'-biphenyl]-3-yl)methyl, 2,2-dichloro-3,3-dimethylcyclopropanecarboxylate, (2,4-dimethyl-[1,1'-biphenyl]-3-yl)methyl 3-cyclopentylidenemethyl-2,2-dimethylcyclopropanecarboxylate, and (2,4-dimethyl-[1,1'-biphenyl]-3-yl)methyl 3-(2-methyl-1-propenyl)-2,2-dimethylcyclopropanecarboxylate.

Insecticidal and acaricidal [1,1'-biphenyl]-3-ylmethyl pyrethroid esters also result when R is selected from Group III, either a or b is 0, and the (A)ₐ or (B)ᵦ substitution pattern is among those described above. Examples of such esters include (2-methyl-[1,1'-biphenyl]-3-yl)methyl, (2,4-dimethyl-[1,1'-biphenyl]-3-yl)methyl, and (2,4,5,6-tetrafluoro[1,1'-biphenyl]-3-yl)methyl 3-(2-chloro-2-phenylethenyl)-2,2-dimethylcyclopropanecarboxylate; (2-methyl-[1,1'-biphenyl]-3-yl)methyl, (2,4-dimethyl-[1,1'-biphenyl]-3-yl)methyl, and (2,4,5,6-tetrafluoro-[1,1'-biphenyl]-3-yl)methyl 4-chloro-α-(1-methylethenyl)benzeneacetate; as well as (2-methyl-[1,1'-biphenyl]-3-yl)methyl, (2,4-dimethyl-[1,1'-biphenyl]-3-yl)methyl, and (2,4,5,6-tetrafluoro-[1,1'-biphenyl]-3-yl)methyl 2,2-dichloro-1-(4-ethoxyphenyl)cyclopropanecarboxylate.

Esters exhibiting systemic insecticidal activity result when R is selected from Groups I, II, III, and IV, b is 0, a is 2–4, and A is fluoro. For systemic activity, it is preferred that R be selected from Groups I, III, and IV, especially I and IV. Specific compounds of interest as systemic insecticides are (2,4,5,6-tetrafluoro-[1,1'- biphenyl]-3-yl)methyl cis-3-(2-chloro-3,3,3-trifluoro-1-propenyl)-2,2-dimethylcyclopropanecarboxylate, (2,4,5,6-tetrafluoro-[1,1'-biphenyl]-3-yl)methyl trans-3-(2,2-dibromoethenyl)-2,2-dimethylcyclopropanecarboxylate, 2,4,5,6-tetrafluoro-[1,1'-biphenyl]-3-yl)methyl cis-3-(2,2-dichloroethenyl)-2,2-dimethylcyclopropanecarboxylate, (2,4,6-trifluoro-[1,1'-biphenyl]-3-yl)methyl cis-3-(2-chloro-3,3,3-trifluoro-1-propenyl)-2,2-dimethylcyclopropanecarboxylate, (2,4,6-trifluoro-[1,1'-biphenyl]-3-yl)methyl cis-3-(2,2-dichloroethenyl)-2,2-dimethylcyclopropanecarboxylate, (2,4,5,6-tetrafluoro-[1,1'-biphenyl]-3-yl)methyl cis-3-(3-chloro-2,3,3-trifluoro-1-propenyl)-2,2-dimethylcyclopropanecarboxylate, (2,4,6-trifluoro-[1,1'-biphenyl]-3-yl)methyl cis-3-(3-chloro-2,3,3-trifluoro-1-propenyl)-2,2-dimethylcyclopropanecarboxylate, (2,6-difluoro-[1,1'-biphenyl]-3-yl)methyl 2,2-dichloro-1-(4-ethoxyphenyl)-cyclopropanecarboxylate, (2,6-difluoro-[1,1'-biphenyl]-3-yl)methyl 1R-cis-3-(2,2-dibromoethenyl)-2,2-dimethylcyclopropanecarboxylate, (2,4,6-trifluoro-[1,1'-biphenyl]-3-yl)methyl 1R-cis-3-(2,2-dichloroethenyl)-2,2-dimethylcyclopropanecarboxylate, and (2,4,6-trifluoro-[1,1'-biphenyl]-3-yl)methyl 1R-cis-3-(2,2-dibromoethenyl)-2,2-dimethylcyclopropanecarboxylate.

Also within the contemplation of this invention are insecticidal and acaricidal compositions comprising an insecticidally or acaricidally effective amount of [1,1'-biphenyl]-3-ylmethyl pyrethroid ester in admixture with an agriculturally acceptable carrier and a method of controlling insects or acarids which comprises applying to the locus where control is desired an insecticidally or acaricidally effective amount of [1,1'-biphenyl]-3-ylmethyl pyrethroid ester. In addition, those [1,1'-biphenyl]-3-ylmethyl pyrethroid esters of Formula I wherein R is selected from Groups I, II, III, and IV, b is 0, a is 2–4, and A is fluoro are employed to control insects which feed on a crop by applying an insecticidally effective amount of at least one of those esters on or in soil contiguous to the crop before, during, or after planting said crop.

The [1,1'-biphenyl]-3-ylmethyl pyrethroid esters of this invention are prepared by reaction between a carbonyl halide, e.g., a chloride, RCOCl, wherein R is selected from Groups I, II, III, or IV above; an acid, RCOOH; an ester, RCOOR', wherein R' is conveniently a $C_1$–$C_6$ alkyl group; an anhydride, RCOOR'', wherein R'' is $C_1$–$C_6$ alkylcarbonyl, or $C_1$–$C_6$ alkyl or aryl sulfonyl; or a nitrile, RCN, and an appropriate [1,1'-biphenyl]-3-methanol. Alternatively, they are prepared by reacting a salt, RCOOM, where M is an alkali or alkaline earth metal, e.g., Li, K, Na, Ca, or Mg, a transition metal, e.g., Ag, or ammonium, or alkyl-substituted ammonium, with a [1,1'-biphenyl]-3-ylmethyl compound wherein the benzylic carbon atom carries a leaving group which is readily displaced by carboxylate anions. Suitable leaving groups are known in the art and include, for example, halogen, especially bromine and chlorine; carboxylate, especially acetate; sulfonate, e.g.,

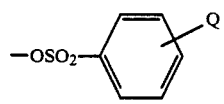

where Q is halogen, especially bromine, $C_1$–$C_6$ alkyl, e.g., p-toluenesulfonate, nitro, or hydrogen, and —O-SO$_2$C$_R$H$_S$F$_T$ where R is 1–4, e.g., methanesulfonate, and S and T are independently 0–9; and —NR$_3$X, where R may be $C_1$–$C_6$ alkyl, and X may be halogen, sulfonate, or other readily available anion. These syntheses, illustrated in Examples 1, 2 and 3 below, are processes of this invention.

3-(2,2-Dichloroethenyl)- and 3-(2,2-dibromoethenyl)-2,2-dimethylcyclopropanecarboxylic acid and corresponding carbonyl chlorides are obtained by methods disclosed in U.S. Pat. No. 4,024,163 and in *Coll. Czech. Chem. Comm.*, 24, 2230 (1959). Carbonyl chlorides or corresponding salts wherein R is 2,2,3,3-tetramethylcyclopropyl, 2,2-dichloro-3,3-dimethylcyclopropyl, 3-cyclopentylidenemethyl-2,2-dimethylcyclopropyl, 3-(2,2-dimethylethenyl)-2,2-dimethylcyclopropyl, 3-(2-chloro-2-phenylethenyl)-2,2-dimethylcyclopropyl, 4-chloro-α-(1-methylethyl)phenylmethyl, and 2,2-dichloro-1-(4-ethoxyphenyl)cyclopropyl are disclosed in *Agr. Biol. Chem.*, 31, 1143 (1967), *Agr. Biol. Chem.*, 38, 1511 (1974), U.S. Pat. No. 3,679,667, *Agr. Biol. Chem.*, 28, 27 (1964), U.S. Pat. No. 4,157,447, *Agr. Biol. Chem.*, 39, 267 (1975), and *Nature*, 272, 734 (1978), respectively. 3-(2-Chloro-3,3,3-trifluoromethyl-1-propenyl)-2,2-dimethylcyclopropanecarboxylic acid and 3-(3-chloro-2,3,3-trifluoromethyl-1-propenyl)-2,2-dimethylcyclopropanecarboxylic acid are disclosed in U.S. Pat. No. 4,238,505. 3-(1,2-Dibromo-2,2-dichloroethyl)-2,2-dimethylcyclopropanecarboxylates are disclosed in U.S. Pat. No. 4,179,575, while U.S. Pat. No. 4,226,802 describes 2-(2-chloro-4-trifluoromethylphenylamino)-3-methylbutanoates. These disclosures are also incorporated herein by reference.

The pure cis or trans cyclopropanecarboxylates are prepared either by reacting pure cis or pure trans cyclopropanecarboxylic acid derivatives with appropriate [1,1'-biphenyl]-3-ylmethyl compounds or by separating cis,trans mixtures using chromatographic techniques. The identities of the cis and trans isomers are established by reference to their nmr spectra, especially the patterns at 5.44–5.71 ppm and 6.10–6.40 ppm for the trans and cis isomers, respectively.

Substituted [1,1'-biphenyl]-3-ylmethyl compounds, which are intermediate in the preparation of many of the insecticidal esters, are novel compositions of matter and are also within the scope of this invention. These intermediates are described by Formula II

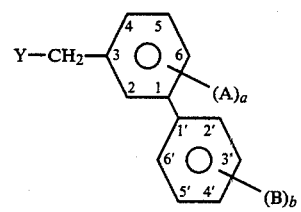

wherein Y is hydroxyl or a leaving group readily displaced by carboxylate anions, and (1) b is 0, a is 1–4, and when a is 1, A is 2- or 6-halo, 4-chloro, 4-fluoro, 5-fluoro, 2-lower alkyl, or 2-trifluoromethyl, and when a is 2, A is fluoro, 2 and 4-substituents independently selected from fluoro, chloro, bromo, and lower alkyl, with the proviso that only one may be bromo or alkyl other than methyl, or 2 and 6-substituents independently selected from fluoro, chloro and methyl, and when a is 3 or 4, A is fluoro, or may be as when a is 1 or a is 2 with one or two additional fluoro groups; or (2) a is 0, b is 1–5, and when b is 1, B is halo, 2' or 3'-lower alkyl, 2' or 3'-trifluoromethyl, or 2' or 3'-lower alkoxy, and when b is 2, B is fluoro, or 2' and 4'-substituents independently selected from fluoro, chloro and bromo, and when b is 3, 4 or 5, B is fluoro; or (3) a is 1–4, b is 1–4, and A is fluoro or a 2-substituent selected from chloro, bromo, and lower alkyl with 0 to 3 fluoro groups, and B is fluoro or a 2'-substituent selected from chloro and methyl with 0 to 3 fluoro groups.

Especially useful are those compounds in which halo is restricted to fluoro and chloro, and lower alkyl is restricted to methyl, especially wherein a is not greater than 3 and b is not greater than 2. Methyl, ethyl, and methoxy, ethoxy are preferred lower alkyl and lower alkoxy substituents respectively. The leaving group, Y, is preferably bromine, chlorine, acetate, p-toluenesulfonate, or methanesulfonate.

Those compounds wherein a is 0 are desirable, especially those containing a single substituent, B, at the 2'-position, most especially fluoro or methyl. When more than one substituent, B, is present, they are preferably halo, especially fluoro. Among those compounds wherein b is 0, it is preferred that A be fluoro or chloro, especially fluoro. When the compound has 2-substitution, it is preferred that it also be substituted at the 4-position when A is halo or lower alkyl. 2-Methyl[1,1'-biphenyl]-3-ylmethyl and 2,4-dimethyl[1,1'-biphenyl]-3-ylmethyl compounds are attractive.

The [1,1'-biphenyl]-3-ylmethyl intermediates are obtained by one or more of several different methods, depending on the specific compounds desired. These methods A-M, are described below. In addition, a [1,1'-biphenyl]-3-methyl alcohol, prepared by one of these methods, can be converted into the corresponding substituted [1,1'-biphenyl]-3-ylmethyl bromide by treating a solution of the alcohol in ether with phosphorous tribromide or phosphorous pentabromide. Similarly, a substituted [1,1-biphenyl]-3-ylmethyl bromide can be converted into the corresponding alcohol by first treating the bromide with sodium acetate in acetic acid, and then treating the thus produced biphenyl acetate with sodium hydroxide in methanol. These techniques are available in the prior art.

Table 1 lists specific examples of [1,1'-biphenyl]-3-ylmethyl pyrethroid esters within the scope of this invention. Table 2 tabulates the physical properties of the exemplary insecticidal esters of Table 1, methods to prepare the [1,1'-biphenyl]-3-ylmethyl intermediates employed in making the esters, and physical properties of the intermediates.

Unless otherwise indicated, all temperatures are in degrees Celsius and pressures are in millimeters of mercury. Proton chemical shifts, taken from nmr spectra in $CDCl_3$, are reported in ppm with respect to tetramethylsilane.

Method A

3-Bromomethyl[1,1'-biphenyl] compounds with (A) substituents are prepared by modification of a diazotization reaction. Thus, the appropriately substituted meta-toluidine is converted to an acetamide, and this is treated with nitrosyl sulfuric acid to give the corresponding nitrosoacetamide, which is subsequently decomposed in benzene to the substituted 3-methylbiphenyl. Treatment with N-bromosuccinimide gives the 3-bromomethyl compound.

For example, to a stirred solution of 2,4-difluoro-3-methylaniline (24.3 g, 0.17 mole) in pyridine (14.1 ml, 0.19 mole) was slowly added acetyl chloride (13.3 ml, 0.19 mole). Upon complete addition, the reaction mixture was stirred at room temperature for 3 hours, then heated for one hour. The reaction mixture was extracted four times with diethyl ether. The combined extracts were washed three times with water, twice with aqueous 2% hydrochloric acid, water, then aqueous 5% sodium bicarbonate, water, and aqueous saturated sodium chloride solution, in that order. The organic layer was dried over magnesium sulfate and filtered. The filtrate was evaporated under reduced pressure, leaving as a solid residue 2,4-difluoro-3-methylacetanilide (27.4 g).

To a stirred solution of 2,4-difluoro-3-methylacetanilide (13.7 g, 0.074 mole) in 300 ml of benzene was added sodium acetate (12.1 g, 0.148 mole). The mixture was cooled to 5°, and nitrosyl hydrogen sulfate (9.4 g, 0.074 mole) was added in one portion. The reaction mixture was stirred for 2 hours at 0°. The reaction mixture was then allowed to warm to room temperature and then heated under reflux for 1.5 hours. The reaction mixture was cooled and washed twice with water, twice with aqueous 10% sodium carbonate, twice with water, twice with aqueous 5% sodium bicarbonate, twice with water, and then with aqueous saturated sodium chloride solution. The organic layer was separated, dried over magnesium sulfate and filtered. The filtrate was evaporated under reduced pressure to a solid residue. The residue was purified by column chromatography on silica gel to give 2,4-difluoro-3-methyl[1,1'-biphenyl] (2.2 g) as an oil.

A stirred solution of 2,4-difluoro-3-methyl[1,1'-biphenyl] (2.2 g, 0.011 mole) and N-bromosuccinimide (1.9 g, 0.011 mole) in 100 ml of carbon tetrachloride was irradiated with a 250 watt brooder lamp for 4 hours. The reaction mixture was allowed to reflux from the heat of the lamp. The reaction mixture was then filtered, and the filter cake was washed with three portions of carbon tetrachloride. The washes and filtrate were combined and evaporated under reduced pressure to give 3-bromomethyl-2,4-difluoro[1,1'-biphenyl] (3.5 g) as an oil whose nmr spectrum was consistent with that expected for the named compound.

In addition to those substituted [1,1'-biphenyl]-3-ylmethyl compounds listed in Table 2 as capable of preparation by this method, 3-bromomethyl-5-fluoro, 3-bromomethyl-6-bromo, 3-bromomethyl-2,5-difluoro, 3-bromomethyl-4,5-difluoro, 3-bromomethyl-4,6-difluoro, 3-bromo-methyl-5,6-difluoro, 3-bromomethyl-2,6-difluoro, 3-bromomethyl-2,4,5-trifluoro, 3-bromomethyl-2,4,6-trifluoro, 3-bromomethyl-4,5,6-trifluoro, and 3-bromomethyl-2,4-dibromo-[1,1'-biphenyl] are also prepared by method A.

EXAMPLE 1

(2,4-Difluoro-[1,1'-biphenyl]-3-yl)methyl 3-(2,2-dichloroethenyl)-2,2-dimethylcyclopropanecarboxylate To a mixture of cis-3-(2,2-dichloroethenyl)-2,2-dimethylcyclopropanecarboxylic acid (2.2 g, 0.11 mole) in 75 ml of heptane was added sodium hydroxide (0.42 g, 0.011 mole) in 5 ml of water. The mixture was shaken until the acid dissolved. The water was then removed by distillation, the volume of the reaction mixture being reduced to 50 ml. To the reaction mixture was added 3-bromomethyl-2,4-difluoro[1,1'-biphenyl] (3.0 g, 0.011 mole) and 0.1 gram of 1,4-diazabicyclo[2.2.2]-octane in 35 ml of acetonitrile. The mixture was heated under reflux for 3 hours. The solvent was then removed by evaporation under reduced pressure, and the residue was partitioned between water and diethyl ether. The ether phase was washed with two portions of aqueous 2% hydrochloric acid, two portions of water, two portions of aqueous 10% sodium carbonate, two portions of water and one portion of aqueous saturated sodium chloride solution in that order. The washed ethereal solution was dried over magnesium sulfate, and the ether was evaporated under reduced pressure. The oily residue was purified by column chromatography on silica gel, elution with hexane. This afforded (2,4-difluoro-[1,1'-biphenyl]-3-yl)methyl cis-3-(2,2-dichloroethenyl)-2,2-dimethylcyclopropanecarboxylate (1.8 g), Example XIV in Table 1.

If desired, the corresponding 3-chloromethyl compound, 3-methyl methanesulfonate, or the 3-methyl-p-toluenesulfonate can be used in the aforesaid process, rather than 3-bromomethyl-2,4-difluoro[1,1'-biphenyl]. In general, a 3-chloromethyl compound is prepared by chlorination of the 3-methyl compound with N-chlorosuccinimide, with thionyl chloride or chlorine under irradiation, or with sulfonyl chloride and a peroxide such as benzoyl peroxide, or by treating the corresponding [1,1'-biphenyl]-3-methanol with thionyl chloride. The corresponding 3-methyl methanesulfonate or 3-methyl-p-toluenesulfonate is prepared by treating the 3-methanol with methanesulfonyl chloride or p-toluenesulfonyl chloride, respectively.

Method B

3-Bromomethyl[1,1'-biphenyl] compounds, especially those with B substituents, are in general prepared by an extension of the Knoevenagel condensation of ethyl acetoacetate with substituted benzaldehydes. The resultant α,β-unsaturated methyl ketone is reduced with sodium borohydride to the alcohol, which is simultaneously dehydrated and dehydrogenated with either sulfur or palladium on charcoal, followed by treatment with N-bromosuccinimide.

For example, with stirring, 2-fluorobenzaldehyde (30.0 g, 0.24 mole), ethyl acetoacetate (63.0 g, 0.48 mole), 1 ml of diethylamine, and 15 ml of ethanol were combined. The exotherm was controlled by cooling the mixture for approximately 2 minutes in an ice bath. The reaction mixture was then stirred at room temperature for 5 days. Each day an additional 1 ml of an ethanolic solution containing 20% diethylamine was added. After 5 days, the solvent was removed from the reaction mixture by evaporation under reduced pressure to give ethyl α,α-diacetyl-β-(2-fluorophenyl)glutarate.

The ethyl α,α-diacetyl-β-(2-fluorophenyl)glutarate was heated under vacuum at 160°–180°/10–15 mm for 1 hr, eliminating carbon dioxide and ethanol and producing 5-(2-fluorophenyl)-3-methyl-4-carbethoxy-2-cyclohexen-1-one. The crude product was distilled under reduced pressure to give 5-(2-fluorophenyl)-3-methyl-4-carbethoxy-2-cyclohexen-1-one (57.3 g); bp, 155°–162°/1.2 mm.

To 5-(2-fluorophenyl)-3-methyl-4-carbethoxy-2-cyclohexen-1-one (57.3 g, 0.21 mole) was added a solution of sodium hydroxide (11.5 g, 0.29 mole) in 35 ml of ethanol and 80 ml of water. The stirred reaction mixture was heated under reflux for 8 hours. The ethanol was removed by evaporation under reduced pressure, and the residue was extracted with diethyl ether. The ether extract was dried over sodium sulfate and filtered. The filtrate was evaporated under reduced pressure to give 5-(2-fluorophenyl)-3-methyl-2-cyclohexen-1-one (42.3 g).

To a stirred mixture of sodium borohydride (2.0 g, 0.05 mole) in 400 ml of ethanol was added in one portion 5-(2-fluorophenyl)-3-methyl-2-cyclohexen-1-one (42.3 g, 0.21 mole) in 50 ml of ethanol. The reaction mixture was heated under reflux for 16 hours. An additional 2.0 g of sodium borohydride was then added to the reaction mixture and heating under reflux continued for an additional 2 hours. Again, 2.0 g of sodium borohydride was added to the reaction mixture and heating under reflux continued for a 2 hour period. The reaction mixture was stirred with ice, then acidified with aqueous 10% hydrochloric acid. The mixture was extracted with diethyl ether, and the ether extract was washed with an aqueous solution saturated with sodium bicarbonate. The organic layer was dried with sodium sulfate and filtered. The filtrate was evaporated under reduced pressure to give 5-(2-fluorophenyl)-3-methyl-2-cyclohexen-1-ol (41.2 g) as an oil.

A mixture of 5-(2-fluorophenyl)-3-methyl-2-cyclohexen-1-ol (16.6 g, 0.08 mole) and sulfur (7.8 g, 0.24 mole) was heated at 180°–230° for 7.5 hours. The reaction mixture then stood at room temperature for approximately 60 hours before it was distilled under reduced pressure to give 2'-fluoro-3-methyl[1,1'-biphenyl].

A mixture of 2'-fluoro-3-methyl[1,1'-biphenyl] (1.1 g, 0.006 mole) and N-bromosuccinimide (1.1 g, 0.006 mole) in 11 ml of carbon tetrachloride was irradiated with white light to afford 3-bromomethyl-2'-fluoro[1,1'-biphenyl] (1.3 g). The nmr spectrum was consistent with that expected for the named compound.

In addition to those [1,1'-biphenyl]-3-ylmethyl compounds listed in Table 2 as capable of preparation by this method, 3-bromomethyl-2'-bromo, 3-bromomethyl-3'-bromo, 3-bromomethyl-4'-bromo, 3-bromomethyl-2'-trifluoromethyl, 3-bromomethyl-3'-lower alkoxy and 3-bromomethyl-2',4'-dibromo[1,1'-biphenyl] are also prepared by method B.

Method C

Alternately, B ring substituted 3-bromomethyl[1,1'-biphenyl] compounds are prepared by the reaction of an appropriately substituted phenyl magnesium bromide with a 3-methylcyclohexanone, followed by dehydration and dehydrogenation with sulfur or palladium on charcoal, to give a substituted 3-methyl[1,1'-biphenyl], which is then treated with N-bromosuccinimide.

For example, magnesium turnings (6.4 g, 0.26 mole) were flame-dried, the containing glassware was cooled, and 3-bromochlorobenzene (50 g, 0.26 mole), in 50 ml of diethyl ether was added. As the reaction began, an additional 200 ml of diethyl ether was added, and the reaction mixture was heated under reflux for 0.5 hour. To the refluxing reaction mixture was added dropwise, during a 0.5 hour period, 3-methylcyclohexanone (29.2 g, 0.26 mole) in 100 ml of diethyl ether. Upon complete addition, the reaction mixture was heated under reflux for an additional 0.5 hour, then poured into 500 ml of ice-water containing 50 ml of hydrochloric acid. The mixture was extracted with three 200 ml portions of diethyl ether. The combined extract was washed twice with 100 ml portions of an aqueous solution saturated with sodium chloride. After separation, the organic layer was dried over sodium sulfate and filtered. The filtrate was evaporated under reduced pressure to an oil. The oil was purified by distillation using a Kugelrohr distilling system at 85°/0.05 mm for 2.5 hours to give 1-(3-chlorophenyl)-3-methylcyclohexan-1-ol (25 g).

A mixture of 1-(3-chlorophenyl)-3-methylcyclohexan-1-ol (25.0 g, 0.11 mole) and sulfur (7.1 g, 0.22 mole) was heated at 250° for 4.5 hours. The reaction mixture then stood at room temperature for approximately 60 hours, and then it was distilled under reduced pressure to give 19.5 grams of distillate; bp, 150°–165°/10 mm. The distillate was chromatographed on silica gel, elution with hexane. The eluent was evaporated under reduced pressure to give 3'-chloro-3-methyl[1,1'-biphenyl] (17.0 g) as an oil. The nmr and the ir spectra of the oil were consistent with the proposed structure.

3'-Chloro-3-methyl[1,1'-biphenyl] (7.0 g, 0.035 mole) and N-bromosuccinimide (6.4 g, 0.035 mole) in 100 ml of carbon tetrachloride were irradiated for 4 hours with white light to afford 3-bromomethyl-3'-chloro[1,1'-biphenyl] (9.2 g). The nmr spectrum was consistent with that expected for the named compound.

Method D (2',3',4',5',6'-Pentafluoro-[1,1'-biphenyl])-3-methanol was prepared as follows: Under an argon atmosphere, methyl 3-iodobenzoate (2.3 g, 0.009 mole) and 2,3,4,5,6-pentafluorophenyl copper (2.0 g, 0.009 mole) were added to 50 ml of toluene. The stirred reaction mixture was heated under reflux for 2 hours, then cooled to room temperature. The mixture was filtered and the filtrate evaporated under reduced pressure to a residual solid. The solid was recrystallized from methanol to give methyl (2',3',4',5',6'-pentafluoro-[1,1'-biphenyl])-3-carboxylate (2.6 g); mp, 104°–106°.

To a stirred suspension of 0.5 g of lithium aluminum hydride in 50 ml of dry tetrahydrofuran, cooled to −78°, was added dropwise methyl (2',3',4',5',6'-pentafluoro-[1,1'-biphenyl])-3-carboxylate (2.6 g, 0.009 mole) in 50 ml of dry tetrahydrofuran. Upon complete addition, the reaction mixture was stirred while warming to room temperature. A solution of 10% water in tetrahydrofuran was then added dropwise to the reaction mixture to destroy excess lithium aluminum hydride. An additional 50 ml of water was then added, and the liquid phases separated. The aqueous layer was washed with two 50 ml portions of diethyl ether. The ether washes were combined with the organic layer from the reaction mixture and dried. The mixture was filtered and the filtrate evaporated under reduced pressure to give (2',3',4',5',6'-pentafluoro-[1,1'-biphenyl])-3-methanol (3.0 g) as an oil, which solidified on standing. The ir spectrum was consistent with the proposed structure.

Method E

3-Bromomethyl-3'-methyl[1,1'-biphenyl] was prepared by treating 3,3'-dimethyl[1,1'-biphenyl] (20.0 g, 0.11 mole) with N-bromosuccinimide (18.9 g, 0.11 mole) in the presence of 0.1 g of benzoyl peroxide in 130 ml of carbon tetrachloride. Irradiation of the reaction mixture with white light afforded 3-bromomethyl-3'-methyl[1,1'-biphenyl] (4.5 g). The nmr and the ir spectra were consistent with the proposed structure.

Method F (2'-Methyl-[1,1'-biphenyl])-3-methanol was prepared as follows: Under a nitrogen atmosphere a stirred mixture of magnesium turnings (3.0 g, 0.12 mole) and 10 ml of 1,2-dibromoethane in 100 ml of dry tetrahydrofuran was heated to 30°. To the stirred mixture was added dropwise 4,5-dihydro-4,4-dimethyl-2-(3-bromophenyl)oxazole (26.9 g, 0.11 mole) in 50 ml of dry tetrahydrofuran. Upon complete addition, the reaction mixture was heated at reflux for 1.5 hours. The so-prepared Grignard reagent was cooled, placed in a dropping funnel, and added dropwise at 0° to a stirred solution of 2-bromotoluene (18.1 g, 0.11 mole) and 0.5 g of bis(1,3-diphenylphosphino)propanenickel(II) chromate in 150 ml of dry tetrahydrofuran. The temperature of the reaction mixture was maintained at 0° throughout the addition. Upon complete addition, the temperature was allowed to rise to 15°, and the reaction mixture was stirred for 16 hours, then heated under reflux for approximately 24 hours. The reaction mixture was cooled and poured into 500 ml of water. The resultant emulsion was broken by pouring small amounts of the mixture into 1000 ml portions of water. Each portion was extracted with two 200 ml portions of toluene. The combined toluene extracts were evaporated under reduced pressure to afford 25 g of oily residue. The combined water layers were divided into three parts, and to each part was added 10 ml of 6N hydrochloric acid. Each part was extracted with toluene. The combined extracts were evaporated under reduced pressure to give an additional 8.8 g of oily residue. The residues were combined and impurities removed by distillation using a Kugelrohr distilling system. The residue was purified by column chromatography on silica gel, producing 4,5-dihydro-4,4-dimethyl-2-(2'-methyl[1,1'-biphenyl]-3-yl)oxazole (7.2 g).

A stirred solution of 10.5 g 4,5-dihydro-4,4-dimethyl-2-(2'-methyl[1,1'-biphenyl]-3-yl)oxazole and 17.8 ml of concentrated sulfuric acid in 250 ml of ethanol was heated at reflux for 16 hours. The reaction mixture was cooled to room temperature and poured into 150 ml of water. The mixture was treated with 250 ml of aqueous 5% sodium bicarbonate and extracted four times with 250 ml portions of diethyl ether. The combined ether extracts were dried over magnesium sulfate and filtered. The filtrate was evaporated under reduced pressure to a residue. The residue was taken up in 150 ml of methylene chloride and filtered. The filtrate was evaporated under reduced pressure, and the solid residue was purified by column chromatography on silica gel to produce ethyl(2'-methyl[1,1'-biphenyl])-3-carboxylate (4.7 g).

To a stirred suspension of 0.6 g of lithium aluminum hydride in 50 ml of dry tetrahydrofuran was added dropwise, during a 20 minute period, 4.7 g of ethyl(2'-methyl-[1,1'-biphenyl])-3-carboxylate in 10 ml of tetrahydrofuran. Upon complete addition, the reaction mixture was heated under reflux for 1.5 hours, then cooled to room temperature. Excess lithium aluminum hydride was destroyed by the addition of a few drops of ethyl acetate. The reaction mixture was poured into water and the mixture extracted with ether. The extract was dried over magnesium sulfate and filtered. The filtrate was evaporated under reduced pressure to an oily residue of (2'-methyl-[1,1'-biphenyl])-3-methanol (3.1 g).

The ir spectrum of the product was consistent with that expected.

EXAMPLE 2

(2'-Methyl-[1,1'-biphenyl]-3-yl)methyl 3-(2,2-dichloroethenyl)-2,2-dimethylcyclopropanecarboxylate To a stirred solution of (2'-methyl-[1,1'-biphenyl])-3-methanol (3.1 g, 0.016 mole) and 2 ml of pyridine in 65 ml of dry toluene was added dropwise cis,trans-3-(2,2-dichloroethenyl)-2,2-dimethylcyclopropanecarbonyl chloride (3.6, 0.010 mole). The reaction mixture was then stirred at room temperature for 16 hours, and then poured into 100 ml of water and shaken. The toluene layer was separated and washed successively with 50 ml of dilute hydrochloric acid, 50 ml of dilute sodium hydroxide solution, and two 300 ml portions of water. The washed toluene layer was dried over magnesium sulfate, and the toluene was removed by evaporation under reduced pressure. The residue was purified by column chromatography on silica gel, elution with 1:1 chloroform:hexane to afford (2'-methyl-[1,1'-biphenyl]-3-yl)methyl cis,trans-3-(2,2-dichloroethenyl)2,2-dimethylcyclopropanecarboxylate (4.9 g), Example XIX in Table 1.

Method G

2-Methyl[1,1'-biphenyl]-3-methanol was prepared as follows: To 100 ml of stirred 50% aqueous ethanol was added 2-methyl-3-nitrobenzyl alcohol (41.8 g, 0.25 mole) and 85.0 grams of iron powder. The mixture was brought to reflux, and 5.2 ml of concentrated hydrochloric acid was slowly added. Upon complete addition, the reaction mixture was stirred under reflux for 2 hours. The reaction mixture was then made just basic with ethanolic 15% potassium hydroxide. The hot mixture was filtered through diatomaceous earth to remove the iron. The filter cake was washed with ethanol. The filtrate was acidified with hydrogen chloride, then allowed to stand at room temperature for 16 hours. The ethanol was removed by evaporation under reduced pressure. Hexane was added to the residue, and the water-hexane azeotrope was removed by distillation. The addition of hexane and the subsequent removal of the water-hexane azeotrope by distillation was repeated three times. The 3-hydroxymethyl-2-methylaniline hydrochloride residue thus obtained was used as follows.

A stirred solution of 3-hydroxymethyl-2-methylaniline hydrochloride (43.4 g, 0.25 mole) and 17.2 ml of concentrated sulfuric acid in ice-water was cooled to 0°, and a solution of sodium nitrite (17.3 g, 0.25 mole) in water was added dropwise. Upon complete addition, the reaction mixture was stirred for an additional 0.5 hour, then an additional 8 ml of concentrated sulfuric acid was added dropwise. With the temperature maintained at 0°, a solution of potassium iodide (49.8 g, 0.30 mole) in water was added dropwise to the reaction mixture, followed by the addition of 0.1 gram of copper powder. The reaction mixture was slowly warmed to 70° where it stirred for 1 hour. The reaction mixture was then allowed to stand for 18 hours while cooling to room temperature. The reaction mixture was then taken up in water and extracted with chloroform. The chloroform extract was washed with an aqueous saturated solution of sodium bisulfite, then with water. The chloroform layer was dried and filtered. The filtrate was evaporated under reduced pressure to give 3-iodo-2-methylbenzyl alcohol (15.2 g) as a dark solid.

In a photoreactor was placed 3-iodo-2-methylbenzyl alcohol (5.0 g, 0.02 mole) and 800 ml of benzene. To this was added sodium thiosulfate (5.0 g, 0.04 mole) in 15 ml of water. The mixture was purged with argon for 30 minutes, then irradiated with a 200 watt medium pressure ultraviolet lamp for 36.5 hours. The reaction mixture was then transferred to a separatory funnel. The photoreactor was washed with approximately 20 ml each of water, chloroform, and acetone. These washes were added to the separatory funnel. The organic layer was washed with aqueous 0.5M sodium thiosulfate, then with an aqueous solution saturated with sodium chloride. The organic layer was then dried and filtered. The filtrate was evaporated under reduced pressure to an oily residue. The residue was purified by column chromatography on silica gel, elution with 1:1 hexane:chloroform, to give 2-methyl[1,1'-biphenyl]-3-methanol (2.4 g). The nmr and ir spectra were consistent with that expected for the named compound.

Method H 2,4-Dimethyl-[1,1'-biphenyl]-3-methanol was prepared as follows:

A solution of 46 ml of concentrated sulfuric acid and 23.5 ml of concentrated nitric acid was added slowly to a stirred solution of 2,6-dimethylbenzoic acid (50.0 g, 0.333 mole) in 200 ml of methylene chloride at a rate such that a gentle reflux was maintained throughout the addition. After complete addition, reflux was maintained for 30 minutes. The reaction mixture was cooled, poured onto 300 g of ice and the organic phase separated. The aqueous phase was extracted with three 200 ml portions of diethyl ether, and the organic phases were combined, dried over anhydrous magnesium sulfate, and filtered. The solvent was removed from the filtrate under reduced pressure to give 2,6-dimethyl-3-nitrobenzoic acid (60.2 g) as a solid.

Under a dry argon atmosphere, a borane-tetrahydrofuran complex (39.7 g, 0.463 mole) as a 1M solution in tetrahydrofuran was added slowly to a stirred solution of 2,6-dimethyl-3-nitrobenzoic acid (60.2 g, 0.308 mole) in 350 ml of anhydrous tetahydrofuran. The reaction mixture was heated at 60° for approximately 18 hours. Water (20 ml) was slowly added to the reaction mixture, and the resultant mixture was concentrated under reduced pressure to give a residue. The residue was washed with three 100 ml portions of methylene chloride, then three 100 ml portions of a 2N aqueous sodium hydroxide. The washes were combined and the organic phase separated. The aqueous phase was washed with four 250 ml portions of methylene chloride, and the organic phases were combined, dried with anhydrous magnesium sulfate, and filtered. The solvent was removed from the filtrate under reduced pressure to give 2,6-dimethyl-3-nitrobenzene-1-methanol (51.3 g, mp 86.5°–88.5°).

A stirred solution of 2,6-dimethyl-3-nitrobenzene-1-methanol (51.3 g, 0.283 mole) and 25 ml of pyridine in 350 ml of toluene was warmed to 70°. During a ten minute period, acetyl chloride (22.2 g, 0.283 mole) was added to the reaction mixture. The reaction mixture was heated at 85° for 2½ hours, then poured over 300 g of ice, and 100 ml of a 4N hydrochloric acid solution was added thereto. The organic phase was separated and washed with 100 ml of aqueous 2N hydrochloric acid, dried over anhydrous magnesium sulfate, and filtered. The solvent was removed from the filtrate under reduced pressure to give (2,6-dimethyl-3-nitrophenyl)methyl acetate (47.5 g) as an oil.

Under a dry argon atmosphere, 0.65 g of 5% platinum on charcoal and 20 ml of methanol were added to a hydrogenation bottle, followed by (2,6-dimethyl-3-nitrophenyl)methyl acetate (22.5 g, 0.100 mole) in 175 ml of methanol. The mixture was hydrogenated for 1½ hours and filtered. The filtrate was concentrated under reduced pressure to give 3-(amino-2,6-dimethylphenyl)methyl acetate as an oil.

Under a dry argon atmosphere (3-amino-2,6-dimethylphenyl)methyl acetate (36.0 g, 0.186 mole) was added to benzene (145.3 g, 1.86 mole), and the measured solution was degassed under reduced pressure. The argon atmosphere was restored, and the solution was heated at reflux for 45 minutes, collecting the azeotroped water in a Dean-Stark trap. During a 1½ hour period, t-butyl nitrite (28.8 g, 0.279 mole) was added to the reaction mixture while maintaining a moderate reflux. Heptane (500 ml) was added to the reaction mixture, and the solvent was removed by distillation. The resultant residue was subjected to column chromatography on silica gel, eluted first with toluene, followed by toluene:methyl chloride (65:35), methylene chloride, and finally ethylacetate:methylene chloride (5:95) to give an oil. The oil was distilled (75°-133°/0.05 mm) to give a low melting solid. The solid was recrystallized from n-heptane and then purified by column chromatography on silica gel, elution with toluene, to give 2,4-dimethyl-[1,1'-biphenyl]-3-methyl acetate (0.95 g) as a solid.

A mixture of 2,4-dimethyl-[1,1'-biphenyl]-3-methyl acetate (0.85 g, 0.0033 mole), potassium hydroxide (0.43 g, 0.0066 mole) and 25 ml of methanol was stirred at room temperature for one hour. The solvent was removed under reduced pressure, and the residue was extracted with approximately 60 ml of a saturated aqueous sodium chloride solution and 30 ml of methylene-chloride. The organic phase was separated, and the aqueous phase was extracted with three 75 ml portions of methylene-chloride. The organic phases were combined, dried with anhydrous magnesium sulfate, and filtered. The filtrate was evaporated under reduced pressure to give an oil. The oil was purified by column chromatography on silica gel, elution with methylene-chloride, to give a low melting solid. The solid was recrystallized from n-heptane to give 2,4-dimethyl-[1,1'-biphenyl]-3-methanol as a white solid (mp 77°-78°).

Analysis: Calc. for $C_{15}H_{15}O$: C, 84.87; H, 7.59; Found: C, 84.25; H, 7.62.

EXAMPLE 3

(2,4-Dimethyl [1,1'-biphenyl]-3-yl)methyl cis-3-(2,2-dichloroethenyl)-2,2-dimethylcyclopropanecarboxylate Under a dry nitrogen atmosphere a stirred solution of 30 ml of toluene, 0.64 ml of pyridine and 2,4-dimethyl-[1,1'-biphenyl]-3-methanol (0.9 g, 0.004 mole) was heated at reflux. During a ten minute period a solution of cis-3-(2,2-dichloroethenyl)-2,2-dimethylcyclopropanecarbonyl chloride (0.91 g, 0.004 mole) in 12 ml of toluene was added to the reaction mixture. The reaction mixture was heated at reflux for 1½ hours, cooled to room temperature and diluted with diethyl ether. The ethereal solution was washed in succession with 20 ml portions of water, 2% aqueous hydrochloric acid, water, 2% aqueous hydrochloric acid, 5% aqueous sodium carbonate, water, 5% aqueous sodium carbonate, water and saturated aqueous sodium chloride. The organic solution was dried over anhydrous magnesium sulfate, filtered and the solvent evaporated under reduced pressure to give an oil.

The oil was purified by preparative chromatography on silica gel, elution with hexane:ethylacetate (95:5), to give (2,4-dimethyl-[1,1'-biphenyl]-3-yl)methyl cis-3-(2,2-dichloroethenyl)-2,2-dimethylcyclopropanecarboxylate, Example XXXVIII in Table 1.

Method I 2,3,4,6-Tetrafluoro-[1,1'-biphenyl]-5-methanol was prepared as follows:

A stirred solution of 2,3,4,6-tetrafluoroaniline (50 g, 0.30 mole) in benzene (236.6 g, 3.03 mole) was heated under reflux. During a 45 minute period, t-butyl nitrite (46.8 g, 0.455 mole) was added to the reaction mixture. After complete addition the mixture was heated at reflux for 2¾ hours. n-Heptane (1 l) was added, and the solvent was distilled from the reaction flask until a head temperature of 101° was reached. The pot residue was cooled and subjected to column chromatography on silica gel, elution first with n-heptane, then toluene, to give 2,3,4,6-tetrafluoro-[1,1'-biphenyl] (mp, 89°-90°).

Under a dry argon atmosphere, a stirred solution of 2,3,4,6-tetrafluoro-[1,1'-biphenyl] (23.0 g, 0.102 mole) in 400 ml of diethyl ether was cooled to −65°. During a 1¼ hour period 63.4 ml of a 1.6M solution of n-butyl lithium in hexane was added to the reaction mixture, which was then stirred at −65° for 2¾ hours. During a one hour period, freshly crushed dry ice (750 g) was added to the mixture. The stirred reaction mixture was then allowed to warm to room temperature. The mixture was cooled; 400 ml of 6N aqueous hydrochloric acid was added and the resultant mixture stirred vigorously for two hours. The mixture was poured into a separatory funnel, the aqueous phase separated and extracted with three 300 ml portions of diethyl ether. The combined extracts were dried over anhydrous magnesium sulfate, filtered, and concentrated under reduced pressure to give a solid residue. The solid was recrystallized from toluene:n-heptane (1:1) to give 2,4,5,6-tetrafluoro-[1,1'-biphenyl]-3-carboxylic acid (mp, 189°-190.5°).

Under a dry argon atmosphere 2,4,5,6-tetrafluoro-[1,1'-biphenyl]-3-carboxylic acid (21.6 g, 0.08 mole) was dissolved in 150 ml of tetrahydrofuran with stirring. During a 45 minute period 6.9 g of a borane-tetrahydrofuran complex (1.00 molar solution in tetrahydrofuran) was added to the reaction mixture. After complete addition, the reaction mixture was stirred at room temperature for approximately 23 hours. Water (5 ml) was added slowly to the reaction mixture, and the resultant mixture was stirred for two hours. The mixture was dried over anhydrous magnesium sulfate and filtered. The filtrate was concentrated under reduced pressure to give a residue, which was dissolved in diethyl ether and water. The organic phase was separated, washed with three 200 ml portions of 2N aqueous sodium hydroxide, and dried over anhydrous magnesium sulfate. Filtration of the mixture and evaporation of the solvent from the filtrate gave 2,4,5,6-tetrafluoro-[1,1'-biphenyl]-3-methanol as an oil.

Analysis: Calc'd for $C_{13}H_8F_4O$: C, 60.94; H, 3.15; Found: C, 60.73; H, 3.13.

2,6-Difluoro and 2,4,6-trifluoro-[1,1'-biphenyl]-5-methanol are also prepared by method I.

Method J

2-Ethyl-[1,1'-biphenyl]-3-methanol was prepared as follows:

During a 45 minute period 3-chloro-2-methylaniline (141.6 g, 1.0 mole) was added to a stirred solution of isoamyl nitrite (175.6 g, 1.5 moles) in benzene (842 g, 10.0 moles). The reaction mixture was stirred at room temperature for two hours, heated at reflux for one hour, then cooled to room temperature. Approximately 2 l of n-heptane was added to the reaction mixture. Most of the solvents were distilled from the mixture under reduced pressure, followed by distillation at atmospheric pressure (until a head temperature of 95° was reached). The pot residue was dissolved in 2 l of n-heptane and the solution filtered through 250 g of silica gel. The filtrate was subjected to column chromatography on 250 g of silica gel, elution with n-heptane, to give an oil. The oil was rechromatographed on 250 g of silica gel, elution with n-heptane, to give an oil. The oil was distilled in a Kugelrohr distillation apparatus (90°/0.05 mm) to give 3-chloro-2-methyl-[1,1'-biphenyl] (23.5 g) as an oil.

A stirred solution of 3-chloro-2-methyl-[1,1'-biphenyl] (13.5 g, 0.067 mole) and N-bromosuccinimide (11.8 g, 0.067 mole) in 125 ml of carbon tetrachloride was irradiated and heated to reflux for 6½ hours with a 250 watt brooder lamp. The light/heat source was turned off and the reaction mixture stirred at room temperature for approximately 64 hours. The reaction mixture was again irradiated and heated for two hours with the brooder lamp. The mixture was cooled, a solid precipitate filtered off, and the filter cake washed with two 50 ml portions of carbon tetrachloride. The filtrate was washed with saturated aqueous sodium chloride solution, dried over anhydrous magnesium sulfate, and filtered. The filtrate was evaporated under reduced pressure to give 2-bromomethyl-3-chloro-[1,1'-biphenyl] as an oil.

A stirred solution of 2-bromomethyl-3-chloro-[1,1'-biphenyl] (18.7 g, 0.067 mole) and hexamethylenetetraamine (9.3 g, 0.067 mole) in 200 ml of chloroform was heated at reflux for 22½ hours. The reaction mixture was cooled and the solvent evaporated under reduced pressure to give a residue. To the residue was added 250 ml of a 1:1 solution of concentrated acetic acid:water. The mixture was heated at reflux for approximately 22 hours, then cooled. The mixture was saturated with sodium chloride and extracted with four 200 ml portions of methylene chloride. The extracts were combined, washed with saturated aqueous sodium chloride solution, followed by saturated aqueous sodium bicarbonate solution, and dried over anhydrous potassium carbonate. The mixture was filtered and the filtrate evaporated under reduced pressure to give a residue. The residue was subjected to column chromatography on silica gel, elution first with toluene:n-heptane (9:1), followed by toluene:methylene chloride (1:1), and finally methylene chloride to give 3-chloro-[1,1'-biphenyl]-2-carboxaldehyde (3.4 g) as an oil.

Under a dry argon atmosphere n-butyllithium (1.3 g, 0.020 mole) was added slowly to a stirred ice cold mixture of (methyl)triphenylphosphonium bromide (7.3 g, 0.0203 mole) in 30 ml of tetrahydrofuran. The mixture was warmed to room temperature, stirred for two hours, and 3-chloro-[1,1'-biphenyl]-2-carboxaldehyde (4.4 g, 0.0203 mole) in 30 ml of tetrahydrofuran added. The reaction mixture was stirred at room temperature for approximately 18 hours, heated at reflux for two hours, then cooled. The reaction mixture was diluted with 300 ml of diethyl ether and washed with 100 ml of water. The organic phase was dried over anhydrous magnesium sulfate, filtered, and evaporated to give a residue. Distillation of the residue at 88°/0.05 mm gave 3-chloro-2-ethenyl-[1,1'-biphenyl] (2.3 g).

The hydrogenation of 2.3 g (0.0107 mole) of 3-chloro-2-ethenyl-[1,1'-biphenyl] in 100 ml of methanol and 0.1 g of 5% palladium on charcoal gave 3-chloro-2-ethyl-[1,1'-biphenyl] (2.3 g).

Under a dry nitrogen atmosphere a mixture of 3-chloro-2-ethyl-[1,1'-biphenyl] (2.3 g, 0.0106 mole), copper cyanide (1.4 g, 0.0016 mole) and pyridine (1.2 g, 0.016 mole) was heated at 195° for approximately 18 hours. The reaction mixture was cooled to room temperature to give a solid. The solid was dissolved in 300 ml of methylene chloride and washed with 25% aqueous ammonium hydroxide and the aqueous phase extracted with 250 ml of methylene chloride. The organic phases were combined, dried over anhydrous magnesium sulfate, and filtered. The filtrate was evaporated to give 2-ethyl-[1,1'-biphenyl]-3-carbonitrile as a solid. A mixture of ethyl-[1,1'-biphenyl]-3-carbonitrile (2.2 g, 0.0106 mole), 40 ml of 10N aqueous sodium hydroxide, and 40 ml of ethanol was heated at reflux for approximately 18 hours. The reaction mixture was cooled and the ethanol evaporated under reduced pressure. The remaining aqueous portion was diluted with 100 ml of water, then extracted with three 150 ml portions of methylene chloride. The organic phases were combined, dried over anhydrous magnesium sulfate, and filtered. The filtrate was evaporated to give 2-ethyl-[1,1'-biphenyl]-3-carboxamide (2.4 g).

A stirred solution of 2-ethyl-[1,1'-biphenyl]-3-carboxamide (2.1 g, 0.0093 mole) and potassium hydroxide (26.3 g, 0.4 mole) in 175 ml of 2-hydroxyethyl ether was heated at 163° for approximately 18 hours. The reaction mixture was cooled and diluted with 150 ml of ice water. The solution was acidified with concentrated hydrochloric acid to form a precipitate. The precipitate was isolated by filtration and dissolved in diethyl ether; the ethereal solution was dried over anhydrous magnesium sulfate and filtered. The filtrate was evaporated to give 2-ethyl-[1,1'-biphenyl]-3-carboxylic acid (2.2 g) as a solid.

To a stirred solution of 2-ethyl-[1,1'-biphenyl]-3-carboxylic acid (2.1 g, 0.0093 mole) in 50 ml of tetrahydrofuran was added dropwise borane-tetrahydrofuran complex (1.6 g, 0.0186 mole). The reaction mixture was stirred at room temperature for approximately 18 hours. Water (6 ml) was slowly added to the reaction mixture and the solvent removed under reduced pressure to give a residue. The residue was dissolved in methylene chloride; the solution was washed with 1N aqueous sodium hydroxide, dried over anhydrous magnesium sulfate, and filtered. The filtrate was evaporated under reduced pressure to give 2-ethyl-[1,1'-biphenyl]-3-methanol (2.1 g) as an oil. The ir and nmr spectra were consistent with the named compound.

Method K

2-Chloro-[1,1'-biphenyl]-3-methanol was prepared as follows:

A stirred solution of 3-methyl-2-nitrobenzoic acid (18.1 g, 0.1 mole) in 150 ml of concentrated sulfuric acid was cooled to −5°. Sodium azide (7.5 g, 0.115 mole) was added portionwise to the reaction mixture. After complete addition the reaction mixture was heated at 55° for three hours, then stirred at room temperature for two days. The reaction mixture was poured into ice water and the resulting solution made alkaline (pH 9) with concentrated ammonium hydroxide. A solid precipitate formed and was collected by filtration to give 3-methyl-2-nitroaniline (15.1 g, mp 105°–108.5°).

During a two hour period isoamyl nitrite (92.43 g, 0.189 mole) was added to a stirred solution of 3-methyl-2-nitroaniline (60.0 g, 0.394 mole) in 352 ml of benzene. The reaction mixture was stirred at room temperature for approximately 18 hours, then heated at 65° for five hours. The reaction mixture was cooled and the solvent removed by distillation under reduced pressure to give an oil. The oil was diluted with n-heptane and the solvent removed by distillation under reduced pressure to give an oil. The oil was slurried with 100 g silica gel in 300 ml of n-heptane for 15 minutes, then allowed to stand for approximately 18 hours. The slurry was filtered and the filter cake rinsed with toluene. The filtrate was subjected to column chromatography on 500 g of silica gel, elution with toluene:n-heptane (15:85), to give an oil. The oil was rechromatographed on 480 g of silica gel, elution with toluene:n-heptane (15:85), to give 3-methyl-2-nitro-[1,1'-biphenyl].

During a 45 minute period 3-methyl-2-nitro-[1,1'-biphenyl] (25.4 g, 0.119 mole) was added portionwise at 30° to a stirred solution of stannous chloride (107.5 g, 0.476 mole) and 150 ml of concentrated hydrochloric acid in enough ethanol to produce a solution. After complete addition the mixture was heated at reflux for 17 hours. The mixture was cooled and made basic (pH 9–10) with 4N aqueous sodium hydroxide, producing a white precipitate. The precipitate was collected by filtration and partitioned between water and methylene chloride. The organic phase was separated, dried over anhydrous magnesium sulfate, and filtered. The filtrate was evaporated to give 3-methyl-[1,1'-biphenyl]-2-amine as a yellow oil.

During a five minute period a solution of 3-methyl-[1,1'-biphenyl]-2-amine (5.8 g, 0.0316 mole) in 15 ml of dry acetonitrile was added to a stirred mixture of anhydrous copper (II) chloride (7.5 g, 0.038 mole) and isoamyl nitrite (5.55 g, 0.0474 mole) in 100 ml of anhydrous acetonitrile. The reaction mixture was stirred at room temperature for two hours, 65° for two hours, then room temperature for two days. The mixture was diluted with 600 ml of 2N aqueous hydrochloric acid and extracted with two 150 ml portions of diethyl ether. The extracts were combined, washed with 200 ml of 2N aqueous hydrochloric acid, and dried over anhydrous magnesium sulfate. The mixture was filtered and the filtrate evaporated under reduced pressure to give an oil. The oil was purified by column chromatography on silica gel to give 2-chloro-3-methyl-[1,1'-biphenyl] (0.4 g).

A stirred solution of 2-chloro-3-methyl-[1,1'-biphenyl] (0.5 g, 0.0023 mole) in 8 ml of carbon tetrachloride was irradiated and heated to reflux with a 250 watt brooder lamp. A small amount of benzoyl peroxide was added and the reaction mixture refluxed for ten minutes. A second portion of benzoyl peroxide (total 0.01 g) was added, followed by N-bromosuccinimide (0.43 g, 0.0024 mole). The stirred reaction mixture was irradiated for 16 hours, then cooled, and then filtered. The filter cake was rinsed with carbon tetrachloride and the combined filtrates washed with aqueous saturated sodium chloride solution. The organic phase was dried over anhydrous magnesium sulfate and filtered. The filtrate was evaporated under reduced pressure to give 3-bromomethyl-2-chloro-[1,1'-biphenyl] (0.6 g) as an oil.

Method L

3-Bromomethyl-2-fluoro-[1,1'-biphenyl] was prepared as follows:

A stirred solution of 3-methyl-[1,1'-biphenyl]-2-amine (7.5 g, 0.041 mole, as prepared in method K) in 20 ml of tetrahydrofuran was cooled to 5°. A solution of 40 ml tetrafluoroboric acid (48–50% solution) in 20 ml of water was added to the cooled reaction mixture, followed by dropwise addition of isoamyl nitrite (6.2 g, 0.053 mole). After complete addition, the reaction mixture was stirred for 15 minutes and filtered. The filter cake was rinsed successively with 50 ml each of 5% aqueous tetrafluoroboric acid, cold methanol, and cold diethyl ether. The filter cake was added to 100 ml of toluene and the mixture stirred and heated at 60° until the solid dissolved and bubbling subsided. The mixture was heated at reflux for 30 minutes, then held at room temperature for two days, causing separation of an oil. The toluene was decanted from the oil and evaporated under reduced pressure to give a second oil, which was purified by column chromatography on silica gel, elution by toluene:n-heptane (6:94), to give 2-fluoro-3-methyl-[1,1'biphenyl].

A stirred solution of 2-fluoro-3-methyl-[1,1'-biphenyl] (1.5 g, 0.00805 mole) in 25 ml of carbon tetrachloride was irradiated and heated at reflux with a 250 watt brooder lamp. Benzoyl peroxide (0.2 g) was added to the reaction mixture, followed by N-bromosuccinimide (1.46 g, 0.00805 mole). After a total of 21 hours of irradiation, the reaction mixture was cooled, filtered, and the filter cake rinsed with carbon tetrachloride. The combined filtrates were washed with saturated aqueous sodium chloride solution. The organic phase was dried over anhydrous magnesium sulfate and filtered. The filtrate was evaporated under reduced pressure to give 3-bromomethyl-2-fluoro-[1,1'-biphenyl] (2.03 g) as an oil.

Method M

2-Bromo-[1,1'-biphenyl]-3-methanol was prepared as follows:

A stirred solution of 2-methyl-6-nitroaniline (75.0 g, 0.493 mole) and 40 ml of hydrobromic acid (48% solution) in 135 ml of water was cooled to 0°. During a one hour period a solution of sodium nitrite (36.2 g, 0.51 mole) in 60 ml of water was added to the reaction mixture. The mixture was suction filtered through a sintered glass funnel, collecting the filtrate in a flask cooled by a dry ice-acetone bath. The filtrate was placed in a jacketed addition funnel cooled by a dry ice-acetone bath. During a five minute period this solution was added to a stirred mixture of cuprous bromide (77.8 g, 0.51 mole) in 165 ml of hydrobromic acid (48% solution). After complete addition, the mixture was stirred at room temperature for approximately 18 hours, heated at reflux for two hours, then steam distilled. The distillate was extracted with methylene chloride and the extract washed with 2N aqueous sodium hydroxide, followed by several portions of saturated aqueous sodium chloride solution. The organic phase was passed through phase separation filter paper and evaporated under reduced pressure to give 1-bromo-2-methyl-6-nitrobenzene (17 g) as a solid.

A stirred solution of 1-bromo-2-methyl-6-nitrobenzene (16.2 g, 0.075 mole) in 200 ml of carbon tetrachloride was irradiated and heated at reflux with a 250 watt brooder lamp. N-bromosuccinimide (13.5 g, 0.075 mole) was added to the refluxing reaction mixture, and the mixture was stirred for approximately 23 hours. The mixture was cooled, filtered, and washed with two 200 ml portions of saturated aqueous sodium chloride solution. The organic phase was passed through phase separation filter paper. The filtrate was evaporated under reduced pressure to give 2-bromo-1-bromomethyl-3-nitrobenzene (20 g).

A stirred solution of 2-bromo-1-bromomethyl-3-nitrobenzene (20.2 g, 0.0685 mole), potassium acetate (10.08 g, 0.103 mole), and tetrabutylammonium chloride (1.5 g) in 150 ml of acetonitrile was heated at reflux for six hours. The reaction mixture was cooled, filtered, and extracted with methylene chloride. The extract was evaporated to give a residue which was redissolved in methylene chloride and washed twice with 150 ml portions of saturated aqueous sodium chloride solution. The organic phase was passed through phase separation filter paper and evaporated to give a dark solid. The solid was purified by column chromatography on silica gel, elution with toluene, to give (2-bromo-3-nitrophenyl)methyl acetate as a yellow solid (9.6 g, mp 60°–63°).

The hydrogenation of (2-bromo-3-nitrophenyl)methyl acetate (9.6 g, 0.035 mole) with 0.42 g of platinum oxide, 2 ml of morpholine, and 200 ml of methanol in a Parr hydrogenator (49 lb. of hydrogen pressure) gave (3-amino-2-bromophenyl)methyl acetate (9.1 g) as a yellow oil.

A stirred solution of (3-amino-2-bromophenyl)methyl acetate (8.5 g, 0.035 mole) in 31.1 ml of benzene was heated at reflux. During a 40 minute period t-butyl nitrite (8.03 ml, 0.07 mole) was added to the reaction mixture. The mixture was refluxed for four hours, then held at room temperature for two days. The solvent was distilled from the reaction mixture under reduced pressure and 100 ml of n-heptane added to the residue. The solvent was removed by distillation under reduced pressure to give (2-bromo-[1,1'-biphenyl])-3-yl)methyl acetate (10.2 g) as an oil.

Under a dry nitrogen atmosphere a stirred solution of methyl(2-bromo-[1,1'-biphenyl])-3-yl)methyl acetate (1.87 g, 0.00612 mole), potassium hydroxide (0.81 g, 0.012 mole) and 2 ml of water in 25 ml of methanol was heated at reflux for three hours, then cooled to room temperature for approximately 18 hours. The solvent was evaporated from the reaction mixture under reduced pressure and the residue dissolved in 200 ml of methylene chloride. The solution was washed with three 150 ml portions of saturated aqueous sodium chloride solution. The organic phase was passed through phase separation filter paper and the filtrate evaporated to give 2-bromo-[1,1'-biphenyl]-3-methanol (1.58 g) as an oil.

Analysis: Calc'd for $C_{13}H_9BrO$: C, 59.33; H, 4.21; Found: C, 58.57; H, 4.09.

TABLE 1

| Ex. | Name of Ester |
|---|---|
| I | (4-Fluoro-[1,1'-biphenyl]-3-yl)methyl cis,trans-3-(2,2-dichloroethenyl)-2,2-dimethylcyclopropanecarboxylate |
| II | (6-Fluoro-[1,1'-biphenyl]-3-yl)methyl cis-3-(2,2-dichloroethenyl)-2,2-dimethylcyclopropanecarboxylate |
| III | (6-Fluoro-[1,1'-biphenyl]-3-yl)methyl trans-3-(2,2-dichloroethenyl)-2,2-dimethylcyclopropanecarboxylate |

TABLE 1-continued

| Ex. | Name of Ester |
|---|---|
| IV | (4-Chloro-[1,1'-biphenyl]-3-yl)methyl cis,trans-3-(2,2-dichloroethenyl)-2,2-dimethylcyclopropanecarboxylate |
| V | (6-Chloro-[1,1'-biphenyl]-3-yl)methyl cis,trans-3-(2,2-dichloroethenyl)-2,2-dimethylcyclopropanecarboxylate |
| VI | (6-Chloro-[1,1'-biphenyl]-3-yl)methyl cis-3-(2,2-dichloroethenyl)-2,2-dimethylcyclopropanecarboxylate |
| VII | (6-Chloro-[1,1'-biphenyl]-3-yl)methyl trans-3-(2,2-dichloroethenyl)-2,2-dimethylcyclopropanecarboxylate |
| VIII | (4-Bromo-[1,1'-biphenyl]-3-yl)methyl cis,trans-3-(2,2-dichloroethenyl)-2,2-dimethylcyclopropanecarboxylate |
| IX | (4-Bromo-[1,1'-biphenyl]-3-yl)methyl cis-3-(2,2-dichloroethenyl)-2,2-dimethylcyclopropanecarboxylate |
| X | (4-Bromo-[1,1'-biphenyl]-3-yl)methyl trans-3-(2,2-dichloroethenyl)-2,2-dimethylcyclopropanecarboxylate |
| XI | (2,4-Dichloro-[1,1'-biphenyl]-3-yl)methyl cis,trans-3-(2,2-dichloroethenyl)-2,2-dimethylcyclopropanecarboxylate |
| XII | (2,4-Dichloro-[1,1'-biphenyl]-3-yl)methyl cis-3-(2,2-dichloroethenyl)-2,2-dimethylcyclopropanecarboxylate |
| XIII | (2,4-Dichloro-[1,1'-biphenyl]-3-yl)methyl trans-3-(2,2-dichloroethenyl)-2,2-dimethylcyclopropanecarboxylate |
| XIV | (2,4-Difluoro-[1,1'-biphenyl]-3-yl)methyl cis-3-(2,2-dichloroethenyl)-2,2-dimethylcyclopropanecarboxylate |
| XV | (3'-Methyl-[1,1'-biphenyl]-3-yl)methyl cis,trans-3-(2,2-dichloroethenyl)-2,2-dimethylcyclopropanecarboxylate |
| XVI | (2',3',4',5',6'-Pentafluoro-[1,1'-biphenyl]-3-yl)methyl cis,trans-3-(2,2-dichloroethenyl)-2,2-dimethylcyclopropanecarboxylate |
| XVII | (2',3',4',5',6'-Pentafluoro-[1,1'-biphenyl]-3-yl)methyl cis-3-(2,2-dichloroethenyl)-2,2-dimethylcyclopropanecarboxylate |
| XVIII | (2',3',4',5',6'-Pentafluoro-[1,1'-biphenyl]-3-yl)methyl trans-3-(2,2-dichloroethenyl)-2,2-dimethylcyclopropanecarboxylate |
| XIX | (2'-Methyl-[1,1'-biphenyl]-3-yl)methyl cis,trans-3-(2,2-dichloroethenyl)-2,2-dimethylcyclopropanecarboxylate |
| XX | (3'-Chloro-[1,1'-biphenyl]-3-yl)methyl cis,trans-3-(2,2-dichloroethenyl)-2,2-dimethylcyclopropanecarboxylate |
| XXI | (3'-Chloro-[1,1'-biphenyl]-3-yl)methyl cis-3-(2,2-dichloroethenyl)-2,2-dimethylcyclopropanecarboxylate |
| XXII | (3'-Chloro-[1,1'-biphenyl]-3-yl)methyl trans-3-(2,2-dichloroethenyl)-2,2-dimethylcyclopropanecarboxylate |
| XXIII | (2'-Fluoro-[1,1'-biphenyl]-3-yl)methyl cis,trans-3-(2,2-dichloroethenyl)-2,2-dimethylcyclopropanecarboxylate |
| XXIV | (3'-Fluoro-[1,1'-biphenyl]-3-yl)methyl cis,trans-3-(2,2-dichloroethenyl)-2,2-dimethylcyclopropanecarboxylate |
| XXV | (3'-Fluoro-[1,1'-biphenyl]-3-yl)methyl cis-3-(2,2-dichloroethenyl)-2,2-dimethylcyclopropanecarboxylate |
| XXVI | (3'-Fluoro-[1,1'-biphenyl]-3-yl)methyl trans-3-(2,2-dichloroethenyl)-2,2-dimethylcyclopropanecarboxylate |
| XXVII | (4'-Fluoro-[1,1'-biphenyl]-3-yl)methyl cis,trans-3-(2,2-dichloroethenyl)-2,2-dimethylcyclopropanecarboxylate |
| XXVIII | (4'-Fluoro-[1,1'-biphenyl]-3-yl)methyl cis-3-(2,2-dichloroethenyl)-2,2-dimethylcyclopropanecarboxylate |
| XXIX | (4'-Fluoro-[1,1'-biphenyl]-3-yl)methyl trans-3-(2,2-dichloroethenyl)-2,2-dimethylcyclopropanecarboxylate |
| XXX | (2'-Chloro-[1,1'-biphenyl]-3-yl)methyl cis,trans-3-(2,2-dichloroethenyl)-2,2-dimethylcyclopropanecarboxylate |
| XXXI | (2'-Chloro-[1,1'-biphenyl]-3-yl)methyl cis-3-(2,2-dichloroethenyl)-2,2-dimethylcyclopropanecarboxylate |
| XXXII | (2'-Chloro-[1,1'-biphenyl]-3-yl)methyl trans-3-(2,2-dichloroethenyl)-2,2-dimethylcyclopropanecarboxylate |
| XXXIII | (3'-Trifluoromethyl-[1,1'-biphenyl]-3-yl)methyl cis,trans-3-(2,2-dichloroethenyl)-2,2-dimethylcyclopropanecarboxylate |
| XXXIV | (2'-Methoxy-[1,1'-biphenyl]-3-yl)methyl cis,trans-3-(2,2-dichloroethenyl)-2,2-dimethylcyclopropanecar- |

TABLE 1-continued

| Ex. | Name of Ester |
|---|---|
| XXXV | (2'-Methoxy-[1,1'-biphenyl]-3-yl)methyl cis-3-(2,2-dichloroethenyl)-2,2-dimethylcyclopropanecarboxylate |
| XXXVI | (2',4'-Dichloro-[1,1'-biphenyl]-3-yl)methyl cis,trans-3-(2,2-dichloroethenyl)-2,2-dimethylcyclopropanecarboxylate |
| XXXVII | (2-Methyl-[1,1'-biphenyl]-3-yl)methyl cis-3-(2,2-dichloroethenyl)-2,2-dimethylcyclopropanecarboxylate |
| XXXVIII | (2,4-Dimethyl-[1,1'-biphenyl]-3-yl)methyl cis-3-(2,2-dichloroethenyl)-2,2-dimethylcyclopropanecarboxylate |
| XXXIX | (2,4-Dimethyl-[1,1'-biphenyl]-3-yl)methyl trans-3-(2,2-dichloroethenyl)-2,2-dimethylcyclopropanecarboxylate |
| XL | (2,4,5,6-Tetrafluoro-[1,1'-biphenyl]-3-yl)methyl cis-3-(2,2-dichloroethenyl)-2,2-dimethylcyclopropanecarboxylate |
| XLI | (2,4,5,6-Tetrafluoro-[1,1'-biphenyl]-3-yl)methyl trans-3-(2,2-dibromoethenyl)-2,2-dimethylcyclopropanecarboxylate |
| XLII | (2-Ethyl-[1,1'-biphenyl]-3-yl)methyl cis-3-(2,2-dichloroethenyl)-2,2-dimethylcyclopropanecarboxylate |
| XLIII | (2-Chloro-[1,1'-biphenyl]-3-yl)methyl cis-3-(2,2-dichloroethenyl)-2,2-dimethylcyclopropanecarboxylate |
| XLIV | (2-Fluoro-[1,1'-biphenyl]-3-yl)methyl cis-3-(2,2-dichloroethenyl)-2,2-dimethylcyclopropanecarboxylate |
| XLV | (2-Bromo-[1,1'-biphenyl]-3-yl)methyl cis-3-(2,2-dichloroethenyl)-2,2-dimethylcyclopropanecarboxylate |
| XLVI | ([1,1'-Biphenyl]-3-yl)methyl 2,2,3,3-tetramethylcyclopropanecarboxylate |
| XLVII | (2-Methyl-[1,1'-biphenyl]-3-yl)methyl 2,2,3,3-tetramethylcyclopropanecarboxylate |
| XLVIII | (2,4-Dimethyl-[1,1'-biphenyl]-3-yl)methyl 2,2,3,3-tetramethylcyclopropanecarboxylate |
| XLIX | (2,4,5,6-Tetrafluoro-[1,1'-biphenyl]-3-yl)methyl 2,2,3,3-tetramethylcyclopropanecarboxylate |
| L | (2-Methyl-[1,1'-biphenyl]-3-yl)methyl 2,2-dichloro-3,3-dimethylcyclopropanecarboxylate |
| LI | (2,4-Dimethyl-[1,1'-biphenyl]-3-yl)methyl 2,2-dichloro-3,3-dimethylcyclopropanecarboxylate |
| LII | ([1,1'-Biphenyl]-3-yl)methyl 1R,trans-3-(cyclopentylidenemethyl)-2,2-dimethylcyclopropanecarboxylate |
| LIII | (2-Methyl-[1,1'-biphenyl]-3-yl)methyl 1R,trans-3-(cyclopentylidenemethyl)-2,2-dimethylcyclopropanecarboxylate |
| LIV | (2,4-Dimethyl-[1,1'-biphenyl]-3-yl)methyl 1R,trans-3-(cyclopentylidenemethyl)-2,2-dimethylcyclopropanecarboxylate |
| LV | (2,4,5,6-Tetrafluoro-[1,1'-biphenyl]-3-yl)methyl 1R,trans-3-(cyclopentylidenemethyl)-2,2-dimethylcyclopropanecarboxylate |
| LVI | ([1,1'-Biphenyl]-3-yl)methyl cis,trans-3-(2-methyl-1-propenyl)-2,2-dimethylcyclopropanecarboxylate |
| LVII | (2,4-Dimethyl-[1,1'-biphenyl]-3-yl)methyl cis,trans-3-(2-methyl-1-propenyl)-2,2-dimethylcyclopropanecarboxylate |
| LVIII | ([1,1'-Biphenyl]-3-yl)methyl cis,trans-3-(2-chloro-2-phenylethenyl)-2,2-dimethylcyclopropanecarboxylate |
| LIX | ([1,1'-Biphenyl]-3-yl)methyl 4-chloro-α-(1-methylethyl)benzeneacetate |
| LX | (2-Methyl-[1,1'-biphenyl]-3-yl)methyl 4-chloro-α-(1-methylethyl)benzeneacetate |
| LXI | (2,4-Dimethyl-[1,1'-biphenyl]-3-yl)methyl 4-chloro-α-(1-methylethyl)benzeneacetate |
| LXII | (2,4,5,6-Tetrafluoro-[1,1'-biphenyl]-3-yl)methyl 4-chloro-α-(1-methylethyl)benzeneacetate |
| LXIII | ([1,1'Biphenyl]-3-yl)methyl 2,2-dichloro-1-(4-ethoxyphenyl)cyclopropanecarboxylate |
| LXIV | (2,4,5,6-Tetrafluoro-[1,1'-biphenyl]-3-yl)methyl 2,2-dichloro-1-(4-ethoxyphenyl)cyclopropanecarboxylate |
| LXV | (2,6-Dimethyl-[1,1'-biphenyl]-3-yl)methyl 3-(2,2-dichloroethenyl)-2,2-dimethylcyclopropanecarboxylate |
| LXVI | (2,2'-Dimethyl-[1,1'-biphenyl]-3-yl)methyl 3-(2,2-dichloroethenyl)-2,2-dimethylcyclopropanecarboxylate |
| LXVII | (2-Fluoro-2'-methyl-[1,1'-biphenyl]-3-yl)methyl 3-(2,2-dichloroethenyl)-2,2-dimethylcyclopropanecarboxylate |
| LXVIII | (2'-Fluoro-2-methyl-[1,1'-biphenyl]-3-yl)methyl 3-(2,2-dichloroethenyl)-2,2-dimethylcyclopropanecarboxylate |
| LXIX | (2',5'-Difluoro-2-methyl-[1,1'-biphenyl]-3-yl)methyl 3-(2,2-dichloroethenyl)-2,2-dimethylcyclopropanecarboxylate |
| LXX | (2,4,5,6-Tetrafluoro-[1,1'-biphenyl]-3-yl)methyl cis-3-(2-chloro-3,3,3-trifluoro-1-propenyl)-2,2-dimethylcyclopropanecarboxylate |
| LXXI | (2,4,6-Trifluoro-[1,1'-biphenyl]-3-yl)methyl cis-3-(2-chloro-3,3,3-trifluoro-1-propenyl)-2,2-dimethylcyclopropanecarboxylate |
| LXXII | (2,4,6-Trifluoro-[1,1'-biphenyl]-3-yl)methyl cis-3-(2,2-dichloroethenyl)-2,2-dimethylcyclopropanecarboxylate |
| LXXIII | (2,4,5,6-Tetrafluoro-[1,1'-biphenyl]-3-yl)methyl cis-3-(3-chloro-2,3,3-trifluoro-1-propenyl)-2,2-dimethylcyclopropanecarboxylate |
| LXXIV | (2,4,6-Trifluoro-[1,1'-biphenyl]-3-yl)methyl cis-3-(3-chloro-2,3,3-trifluoro-1-propenyl)-2,2-dimethylcyclopropanecarboxylate |
| LXXV | (2,6-Difluoro-[1,1'-biphenyl]-3-yl)methyl 2,2-dichloro-1-(4-ethoxyphenyl)cyclopropanecarboxylate |
| LXXVI | (2,6-Difluoro-[1,1'-biphenyl]-3-yl)methyl 1R-cis-3-(2,2-dibromoethenyl)-2,2-dimethylcyclopropanecarboxylate |
| LXXVII | (2,4,6-Trifluoro-[1,1'-biphenyl]-3-yl)methyl 1R—cis-3-(2,2-dichloroethenyl)-2,2-dimethylcyclopropanecarboxylate |
| LXXVIII | (2,4,6-Trifluoro-[1,1'-biphenyl]-3-yl)methyl 1R—cis-3-(2,2-dibromoethenyl)-2,2-dimethylcyclopropanecarboxylate |
| LXXIX | (2,6-Difluoro-[1,1'-biphenyl]-3-yl)methyl cis-3-(2,2-dichloroethenyl)-2,2-dimethylcyclopropanecarboxylate |
| LXXX | (2,6-Difluoro-[1,1'-biphenyl]-3-yl)methyl 1R—cis-3-(2,2-dichloroethenyl)-2,2-dimethylcyclopropanecarboxylate |
| LXXXI | (2,6-Difluoro-[1,1'-biphenyl]-3-yl)methyl cis-3-(2-methyl-1-propenyl)-2,2-dimethylcyclopropanecarboxylate |
| LXXXII | (2,6-Difluoro-[1,1'-biphenyl]-3-yl)methyl 1R—trans-3-(cyclopentylidenemethyl)-2,2-dimethylcyclopropanecarboxylate |
| LXXXIII | (2,4,6-Trifluoro-[1,1'-biphenyl]-3-yl)methyl 1R—trans-3-(cyclopentylidenemethyl)-2,2-dimethylcyclopropanecarboxylate |
| LXXXIV | (2,4,6-Trifluoro-[1,1'-biphenyl]-3-yl)methyl 2,2,3,3-tetramethylcyclopropanecarboxylate |
| LXXXV | 2,6-Difluoro-[1,1'-biphenyl]-3-yl)methyl 4-chloro-α-(1-methylethyl)-benzeneacetate |
| LXXXVI | (2,4,5,6-Tetrafluoro-[1,1'-biphenyl]-3-yl)methyl cis-3-(2-methyl-1-propenyl)-2,2-dimethylcyclopropanecarboxylate |
| LXXXVII | (2,4,6-Trifluoro-[1,1'-biphenyl]-3-yl)methyl cis-3-(2-methyl-1-propenyl)-2,2-dimethylcyclopropanecarboxylate |
| LXXXVIII | (2,6-Difluoro-[1,1'-biphenyl]-3-yl)methyl 2,2,3,3-tetramethylcyclopropanecarboxylate |
| LXXXIX | (2,4,5,6-Tetrafluoro-[1,1'-biphenyl]-3-yl)methyl 2,2-dichloro-3,3-dimethylcyclopropanecarboxylate |
| XC | (2,6-Difluoro-[1,1'-biphenyl]-3-yl)methyl 2,2-dichloro-3,3-dimethylcyclopropanecarboxylate |
| XCI | (2,4,6-Trifluoro-[1,1'-biphenyl]-3-yl)methyl 2,2-dichloro-3,3-dimethylcyclopropanecarboxylate |
| XCII | (2,4,6-Trifluoro-[1,1'-biphenyl]-3-yl)methyl 2,2-dichloro-1-(4-ethoxyphenyl)cyclopropanecarboxylate |
| XCIII | 2,4,6-Trifluoro-[1,1'-biphenyl]-3-yl)methyl 4-chloro-α-(1-methylethyl)benzeneacetate |
| XCIV[a] | (2-Methyl[1,1'-biphenyl]-3-yl)methyl cis-3-(1,2-dibromo-2,2-dichloroethyl)-2,2-dimethylcyclopropanecarboxylate Isomers I & II |
| XCV[a] | (2-Methyl[1,1'-biphenyl]-3-yl)methyl cis-3-(1,2-dibromo-2,2-dichloroethyl)-2,2-dimethylcyclopropanecarboxylate Isomer I |
| XCVI[a] | (2-Methyl[1,1'-biphenyl]-3-yl)methyl cis-3-(1,2-dibromo-2,2-dichloroethyl)-2,2-dimethylcyclopropanecarboxylate Isomer II |
| XCVII[a] | (2,4-Dimethyl[1,1'-biphenyl]-3-yl)methyl 1R,cis-3-(1,2-dibromo-2,2-dichloroethyl)-2,2-dimethylcyclo- |

TABLE 1-continued

| Ex. | Name of Ester |
|---|---|
| XCVIII[a] | propanecarboxylate Isomers I & II (2-Methyl[1,1'-biphenyl]-3-yl)methyl 1R,cis-3-(1,2-dibromo-2,2-dichloroethyl)-2,2-dimethylcyclopropane-carboxylate Isomers I & II |
| XCIX | (2-Methyl[1,1'-biphenyl]-3-yl)methyl 2-(2-chloro-4-trifluoromethylphenylamino)-3-methylbutanoate |
| C | (2,4-Dimethyl[1,1'-biphenyl]-3-yl)methyl 2-(2-chloro-4-trifluoromethylphenylamino)-3-methylbutanoate |

[a]Diastereomers are designated Isomer 1 and Isomer II.

TABLE 2

| Ex. | Meth Of Prep | Intermediate Alcohol or Bromide nmr Spectrum, 3-ylmethyl protons only all (s,3H) | % cis | % trans | Calc. C | Calc. H | Found C | Found H |
|---|---|---|---|---|---|---|---|---|
| I | A | 4.60 | 32 | 68 | 64.13 | 4.87 | 64.23 | 4.87 |
| II | A | 4.60 | 100 | | 64.13 | 4.87 | 64.37 | 5.02 |
| III | A | | | 100 | 64.13 | 4.87 | 64.14 | 4.99 |
| IV | A | 4.82 | 37 | 63 | 61.56 | 4.67 | 61.33 | 4.65 |
| V | A | 4.43 | 44 | 56 | 61.56 | 4.67 | 61.68 | 4.76 |
| VI | A | | 100 | | 61.56 | 4.67 | 61.64 | 4.64 |
| VII | A | | | 100 | | | | |
| VIII | A | 4.63 | 53 | 47 | 55.54 | 4.21 | 55.67 | 4.06 |
| IX | A | | 100 | | 55.54 | 4.21 | 55.45 | 4.23 |
| X | A | | | 100 | | | | |
| XI | A | 4.83 | 44 | 56 | 56.79 | 4.08 | 56.74 | 4.17 |
| XII | A | | 100 | | | | | |
| XIII | A | | | 100 | | | | |
| XIV | A | 4.56 | 100 | | 61.38 | 4.41 | 61.01 | 4.37 |
| XV | E | 4.48 | 60 | 40 | 67.85 | 5.71 | 67.21 | 5.96 |
| XVI | D | | 40 | 60 | 54.21 | 3.25 | 54.81 | 3.47 |
| XVII | D | | 100 | | 54.21 | 3.25 | 54.80 | 3.64 |
| XVIII | D | | | 100 | 54.21 | 3.25 | 55.11 | 3.52 |
| XIX | F | | 33 | 67 | 67.86 | 5.71 | 67.64 | 5.72 |
| XX | C | 4.47 | 50 | 50 | 61.56 | 4.67 | 60.70 | 4.56 |
| XXI | C | | 100 | | 61.56 | 4.67 | 61.43 | 4.91 |
| XXII | C | | | 100 | | | | |
| XXIII | B | 4.50 | 50 | 50 | 64.13 | 4.80 | 64.42 | 4.69 |
| XXIV | C | 4.48 | 46 | 54 | 64.13 | 4.87 | 63.99 | 4.63 |
| XXV | C | | 100 | | | | | |
| XXVI | C | | | 100 | | | | |
| XXVII | C | | 27 | 73 | | | | |
| XXVIII | C | | | | | | | |
| XXIX | C | | | 100 | 64.13 | 4.80 | 64.42 | 4.69 |
| XXX | B | 4.50 | 52 | 48 | 61.56 | 4.67 | 60.36 | 4.49 |
| XXXI | B | | 100 | | 61.56 | 4.67 | 61.61 | 4.75 |
| XXXII | B | | | 100 | | | | |
| XXXIII | B | 4.57 | 48 | 52 | 59.61 | 4.32 | 59.21 | 4.19 |
| XXXIV | B | 4.49 | 54 | 46 | 65.19 | 5.47 | 65.32 | 5.39 |
| XXXV | B | | 100 | | | | | |
| XXXVI | B | | 63 | 37 | 56.79 | 4.08 | 57.36 | 4.73 |
| XXXVII | G | 4.70 | 100 | | | | | |
| XXXVIII | H | 4.70 | 100 | | 68.49 | 6.00 | 68.17 | 5.80 |
| XXXIX | H | | | 100 | 68.49 | 6.00 | 65.04 | 6.00 |
| XL | I | 4.82 | 100 | | 56.40 | 3.60 | 56.19 | 3.88 |
| XLI | I | | | 100 | 47.04 | 3.01 | 46.67 | 2.91 |
| XLII | J | 4.80 | 100 | | 68.49 | 5.99 | 70.09 | 6.21 |
| XLIII | K | 4.50 | 100 | | 61.56 | 4.67 | 56.68 | 4.41 |
| XLIV | L | 4.52 | 100 | | 64.13 | 4.87 | 63.70 | 4.60 |
| XLV | M | 4.83 | 100 | | 55.53 | 4.22 | 56.30 | 4.72 |
| XLVI | * | | | | 81.79 | 7.84 | 82.11 | 7.65 |
| XLVII | G | | | | 81.95 | 8.13 | 84.14 | 8.46 |
| XLVIII | H | | | | 82.10 | 8.39 | 81.47 | 8.27 |
| XLIX | I | | | | 66.31 | 5.24 | 66.23 | 5.03 |
| L | G | | | | 66.13 | 5.54 | 66.19 | 5.46 |
| LI | H | | | | 66.85 | 5.88 | 67.15 | 5.83 |
| LII | * | | | 100 | 87.16 | 8.19 | 84.78 | 8.05 |
| LIII | G | | | 100 | 83.38 | 8.07 | | |
| LIV | H | | | 100 | 83.46 | 8.29 | 83.55 | 8.23 |
| LV | I | | | 100 | 69.44 | 5.59 | 70.03 | 5.77 |
| LVI | * | | | | 82.60 | 7.83 | 81.90 | 7.78 |
| LVII | H | | 45 | 55 | 82.83 | 8.34 | 83.24 | 8.11 |
| LVIII | * | | 40 | 60 | 77.78 | 6.04 | 76.84 | 6.08 |
| LIX | * | | | | 76.08 | 6.11 | 75.91 | 6.16 |
| LX | G | | | | 76.42 | 6.41 | 76.80 | 6.86 |
| LXI | H | | | | 76.74 | 6.69 | 76.65 | 6.41 |
| LXII | I | | | | 63.94 | 4.24 | 64.36 | 4.00 |
| LXIII | * | | | | 68.03 | 5.02 | 68.28 | 4.79 |
| LXIV | I | | | | 58.49 | 3.53 | 58.68 | 3.67 |
| LXX | I | | | 100 | 54.96 | 3.35 | 55.01 | 3.48 |
| LXXI | I | | | 100 | 57.10 | 3.70 | 57.40 | 3.91 |
| LXXII | I | | | 100 | 58.76 | 3.99 | 58.46 | 4.05 |

TABLE 2-continued

| | | | | | | |
|---|---|---|---|---|---|---|
| LXXIII | I | 100 | 54.96 | 3.35 | 56.19 | 4.22 |
| LXXIV | I | 100 | 57.09 | 3.69 | 57.60 | 3.62 |
| LXXV | I | | 62.78 | 4.42 | 69.20 | 4.49 |
| LXXVI | I | 100 | 50.43 | 3.62 | 51.31 | 3.89 |
| LXXVII | I | 100 | 58.76 | 3.99 | 58.04 | 4.28 |
| LXXVIII | I | 100 | 48.68 | 3.30 | 52.12 | 4.13 |

*[1,1'-Biphenyl]-3-ylmethanol was prepared by the method of G. S. Hammond and C. E. Reeder, J. Am. Chem. Soc., 80, 573 (1958).

Ester Identifying Properties
nmr Spectrum

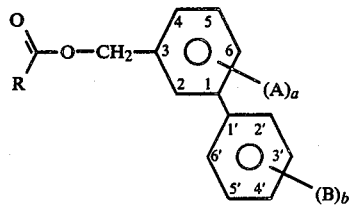

| Ex. | |
|---|---|
| I | 1.17(s,3H); 1.23(s,3H); 1.27(s,3H); 1.30(s,3H); 1.57–2.38(m,4H); 5.23(bs,4H); 5.52–5.65(d,1H); 6.17–6.33(dd,1H); 6.95–7.65(m,16H) |
| II | 1.22(s,3H); 1.25(s,3H); 1.77–2.17(m,2H); 5.08(s,2H); 6.15–6.30(dd,1H); 6.92–7.57(m,8H) |
| III | 1.17(s,3H); 1.27(s,3H); 1.65–1.58(d,1H); 2.12–2.35(dd,1H); 5.10(s,2H); 5.48–5.60(d,1H); 6.91–7.53(m,8H) |
| IV | 1.15(s,3H); 1.20(s,3H); 1.25(s,3H); 1.27(s,3H); 1.63–2.39(m,4H); 5.26(s,2H); 5.28(s,2H); 5.50–5.67(d,1H); 6.20–6.37(dd,1H); 7.17–7.62(m,16H) |
| V | 1.13(s,3H); 1.20(s,3H); 1.23(s,3H); 1.27(s,3H); 1.40–2.35(m,4H); 5.10(s,2H); 5.13(s,2H); 5.52–5.67(d,1H); 6.15–6.30(dd,1H); 7.13–7.51(m,16H) |
| VI | 1.21(s,3H); 1.27(s,3H); 1.77–2.20(m,2H); 5.10(s,2H); 6.17–6.33(dd,1H); 7.13–7.52(m,8H) |
| VII | 1.17(s,3H); 1.27(s,3H); 1.58–1.68(d,1H); 2.13–2.37(dd,1H); 5.13(s,2H); 5.55–5.67(d,1H; 7.03–7.42(m,8H) |
| VIII | 1.17(s,3H); 1.23(s,3H); 1.25(s,3H); 1.28(s,3H); 1.63–2.40(m,4H); 5.25(s,2H); 5.28(s,2H); 5.55–5.68(d,1H); 6.20–6.35(dd,1H); 7.21–7.70(m,16H) |
| IX | |
| X | 1.18(s,3H); 1.30(s,3H); 1.66–1.73(d,2H); 2.18–2.42(dd,2H); 5.30(s,2H); 5.57–5.70(d,1H); 7.25–7.72(m,8H) |
| XI | 1.15(s,3H); 1.20(s,3H); 1.25(s,3H); 1.28(s,3H); 1.58–2.37(m,4H); 5.47(s,2H); 5.50(s,2H); 5.57–5.67(d,1H); 6.20–6.37(dd,1H); 7.13–7.43(m,14H) |
| XII | 1.20(s,3H); 1.26(s,3H); 1.77–2.18(m,2H); 5.50(s,2H); 6.21–6.37(dd,1H); 7.13–7.43(m,7H) |
| XIII | 1.16(s,3H); 1.30(s,3H); 1.59–1.67(d,1H); 2.17–2.39(dd,1H); 5.52(s,2H); 5.55–5.70(d,1H); 7.13–7.50(m,7H) |
| XIV | 1.18(s,3H); 1.25(s,3H); 1.72–2.14(m,2H); 5.18–5.25(t,2H); 6.17–6.28(dd,1H); 6.74–7.55(m,7H) |
| XV | 1.13(s,3H); 1.20(s,3H); 1.26(s,3H); 1.28(s,3H); 1.57–2.36(m,4H); 2.36(s,6H); 5.09(s,2H); 5.13(s,2H); 5.45–5.60(d,1H); 6.17–6.37(dd,1H); 6.95–7.50(m,16H) |
| XVI | 1.17(s,3H); 1.24(s,6H); 1.27(s,3H); 1.57–2.33(m,4H); 5.13(s,4H); 5.47–5.60(d,1H); 6.10–6.25(dd,1H); 6.78–7.46(m,8H) |
| XVII | 1.23(s,6H); 1.78–2.18(m,2H); 5.17(s,2H); 6.15–6.30(dd,1H); 7.03–7.51(m,4H) |
| XVIII | 1.17(s,3H); 1.30(s,3H); 1.57–1.67(d,1H); 2.10–2.33(dd,1H); 5.17(s,2H); 5.50–5.63(d,1H); 6.83–7.48(m,4H) |
| XIX | 1.17(s,3H); 1.20(s,3H); 1.23(s,3H); 1.25(s,3H); 1.57–2.35(m,4H); 2.25(s,6H); 5.10(s,2H); 5.15(s,2H); 5.48–5.61(d,1H); 6.15–6.30(dd,1H); 7.07–7.51(m,16H) |
| XX | 1.17(s,3H); 1.23(s,3H); 1.26(s,3H); 1.30(s,3H); 1.62–2.40(m,4H); 5.17(s,2H); 5.21(s,2H); 5.57–5.68(d,1H); 6.22–6.38(dd,1H); 7.23–7.63(m,16H) |
| XXI | 1.23(s,3H); 1.26(s,3H); 1.80–2.20(m,2H); 5.18(s,2H); 6.20–6.37(dd,1H); 7.23–7.60(m,8H) |
| XXII | 1.17(s,3H); 1.32(s,3H); 1.63–1.73(d,1H); 2.17–2.40(dd,1H); 5.22(s,2H); 5.57–5.70(d,1H); 7.25–7.60(m,8H) |
| XXIII | 1.17(s,3H); 1.23(bs,6H); 1.25(s,3H); 1.58–2.23(m,4H); 5.13(bs,4H); 5.48–5.63(d,1H); 6.13–6.30(dd,1H); 6.81–7.48(m,16H) |
| XXIV | 1.13(s,3H); 1.20(s,3H); 1.23(s,3H); 1.27(s,3H); 1.57–2.34(m,4H); 5.10(s,2H); 5.13(s,2H); 5.47–5.61(d,1H); 6.15–6.30(dd,1H); 6.77–7.45(m,8H) |
| XXV | |
| XXVI | 1.17(s,3H); 1.30(s,3H); 1.63–1.71(d,1H); 2.18–2.42(dd,1H); 5.22(s,2H); 5.57–5.71(d,1H); 6.83–7.57(m,8H) |

TABLE 2-continued

| | |
|---|---|
| XXVII | 1.13(s,3H); 1.20(s,3H); 1.23(s,3H); 1.26(s,3H); 1.57–2.33(m,4H); 5.07(s,2H); 5.12(s,2H); 5.44–5.58(d,1H); 6.10–6.27(dd,1H); 6.85–7.55(m,16H) |
| XXVIII | |
| XXIX | 1.17(s,3H); 1.32(s,3H); 1.63–1.71(d,1H); 2.17–2.40(dd,1H); 5.21(s,2H); 5.54–5.70(d,1H); 6.93–7.63(m,8H) |
| XXX | 1.16(s,3H); 1.22(s,3H); 1.25(s,3H); 1.28(s,3H); 1.60–2.39(m,4H); 5.17(s,2H); 5.20(s,2H); 5.53–5.68(d,1H); 6.20–6.37(dd,1H); 7.17–7.58(m,16H) |
| XXXI | 1.22(s,3H); 1.23(s,3H); 1.76–2.20(m,2H); 5.17(s,2H); 6.20–6.36(dd,1H); 7.15–7.43(m,8H) |
| XXXII | 1.17(s,3H); 1.30(s,3H); 1.62–1.72(d,1H); 2.17–2.40(dd,1H); 5.22(s,2H); 5.57–5.70(d,1H); 7.27–7.43(m,8H) |
| XXXIII | 1.17(s,3H); 1.23(s,3H); 1.27(s,3H); 1.30(s,3H); 1.62–2.40(m,4H); 5.19(s,2H); 5.23(s,2H); 5.55–5.70(d,1H); 6.23–6.37(dd,1H); 7.23–7.83(m,16H) |
| XXXIV | 1.13(s,3H); 1.22(s,3H); 1.58–2.33(m,4H); 3.73(s,6H); 5.08(s,2H); 5.12(s,2H); 5.45–5.60(d,1H); 6.13–6.30(d,1H); 6.77–7.46(m,16H) |
| XXXV | 1.18(s,3H); 1.27(s,3H); 1.68–2.16(m,2H); 3.73(s,6H); 5.13(s,2H); 6.23–6.40(dd,1H); 6.80–7.50(m,7H) |
| XXXVI | 1.15(s,3H); 1.25(s,3H); 1.27(s,3H); 1.30(s,3H); 1.60–2.39(m,4H); 5.15(s,2H); 5.18(s,2H); 5.53–5.67(d,1H); 6.18–6.34(dd,1H); 7.17–7.53(m,7H) |
| XXXVII | 1.24(s,3H); 1.27(s,3H); 1.68–2.21(m,2H); 2.21(s,1H); 5.19(s,2H); 6.18–6.33(dd,1H); 7.19–8.40(m,8H) |
| XXXVIII | 1.20(s,3H); 1.25(s,3H); 1.88–2.00(m,2H); 2.23(s,3H); 2.40(s,3H); 5.27(s,2H); 6.23–6.37(dd,1H); 7.07–7.57(m,7H) |
| XXXIX | 1.18(s,3H); 1.32(s,3H); 1.59–2.45(m,2H); 2.30(s,3H); 2.45(s,3H); 5.32(s,2H); 5.53–5.68(dd,1H); 7.17–7.37(m,7H) |
| XL | 1.23(s,3H); 1.27(s,3H); 1.52–2.32(m,2H); 5.23(s,2H); 6.17–6.32(dd,1H); 7.43(s,5H) |
| XLI | 1.18(s,3H); 1.28(s,3H); 1.6–1.68(d,1H); 2.09–2.32(dd,1H); 5.27(s,2H); 6.10–6.22(d,1H); 7.43(s,5H) |
| XLII | 1.23(s,3H); 1.28(s,3H); 1.73–2.30(m,2H); 5.27(s,2H); 6.23–6.40(dd,1H); 7.10–7.50(m,8H) |
| XLIII | 1.30(s,6H); 1.88–2.27(m,2H); 5.25(s,2H); 6.22–6.35(dd,1H); 7.20–7.37(m,8H) |
| XLIV | 1.23(s,3H); 1.27(s,3H); 1.70–2.60(m,2H); 5.23–5.27(d,2H); 6.21–6.37(dd,1H); 7.03–7.37(m,8H) |
| XLV | 1.20(s,3H); 1.23(s,3H); 1.87–2.25(m,2H); 5.30(s,2H); 6.23–6.37(dd,1H); 7.22–7.4(m,8H) |
| XLVI | 1.17(s,6H); 1.30(s,7H); 5.13(s,2H); 7.23–7.67(m,9H) |
| XLVII | 0.95(s,6H); 1.03(s,6H); 1.53(s,1H); 2.19(s,3H); 5.13(s,2H); 7.06–7.47(m,8H) |
| XLVIII | 1.17(s,6H); 1.30(s,7H); 2.27(s,3H); 2.43(s,3H); 5.27(s,2H); 7.17–7.37(m,7H) |
| XLIX | 1.17(s,6H); 1.25(s,7H); 5.20(s,2H); 7.43(s,5H) |
| L | 1.47(s,3H); 1.50(s,3H); 2.19(s,1H); 2.23(s,3H); 5.27(s,2H); 7.17–7.43(m,8H) |
| LI | 1.43(s,3H); 1.50(s,3H); 2.15(s,1H); 2.28(s,3H); 2.45(s,3H); 5.33(s,2H); 7.07–7.45(m,7H) |
| LII | 1.13(s,3H); 1.30(s,3H); 1.44–1.80(m,6H); 1.97–2.40(m,4H); 4.90–5.42(m,1H); 5.20(s,2H); 7.17–7.67(m,9H) |
| LIII | 1.13(s,3H); 1.33(s,3H); 1.64–1.82(m,6H); 1.93–2.35(m,4H); 2.24(s,3H); 4.93–5.43(m,1H); 5.20(s,2H); 7.10–7.43(m,8H) |
| LIV | 1.13(s,3H); 1.28(s,3H); 1.40–1.83(m,6H); 1.93–2.46(m,4H); 2.27–2.43(d,6H); 4.87–5.40(m,1H); 5.27(s,2H); 7.07–7.47(m,7H) |
| LV | 1.13(s,3H); 1.27(s,3H); 1.37–2.50(m,10H); 4.83–5.47(m,1H); 5.23(s,2H); 7.42(s,5H) |
| LVI | 1.10(s,3H); 1.20(s,3H); 1.25(s,3H); 1.27(s,3H); 1.40–2.40(m,4H); 1.70(bs,12H); 4.78–5.50(m,2H); 5.13(s,2H); 5.17(s,2H); 7.13–7.67(m,18H) |
| LVII | 1.07–1.30(m,12H); 1.2–2.2(m,4H); 1.6–1.8(m,12H); 5.23(s,2H); 5.27(s,2H); 7.10–7.50(m,16H) |
| LVIII | 1.18(s,3H); 1.22(s,3H); 1.33(s,3H); 1.37(s,3H); 1.53–2.73(m,4H); 5.13(s,2H); 5.20(s,2H); 5.63–5.90(dd,1H); 6.30–6.53(m,1H); 7.13–7.67(m,28H) |
| LIX | 0.63–1.07(dd,6H); 2.0–2.5(m,1H); 3.13–3.30(d,1H); 5.13(s,2H); 7.23–7.53(m,9H) |
| LX | 0.65–1.08(dd,6H); 1.93–2.57(m,1H); 2.06(s,3H); 3.13–3.30(d,1H); 5.18(s,2H); 7.17–7.47(m,12H) |
| LXI | 0.63–0.75(d,3H); 0.97–1.08(d,3H); 2.15–2.33(d,6H); 2.0–2.66(m,1H); 3.10–3.27(d,1H); 5.27(s,2H); 7.1–7.5(m,11H) |
| LXII | 0.66–1.07(dd,6H); 2.0–2.63(m,1H); 3.10–3.23(d,1H); 5.23(bs,2H); 7.25–7.40(m,9H) |
| LXIII | 1.27–1.50(t,3H); 1.94–2.10(d,1H); 2.51–2.67(d,1H); 3.77–4.16(q,2H); 5.21(s,2H); 6.77–7.44(m,13H) |
| LXIV | 1.27–1.50(t,3H); 1.97–2.05(d,1H); 2.50–2.63(d,1H); 3.83–4.20(q,2H); 5.27(s,2H); 6.68–7.40(m,9H) |
| LXX | 1.30(s,6H); 1.77–2.34(m,2H); 5.23–5.28(m,2H); 6.83(d,1H); 7.47(s,5H) |

TABLE 2-continued

| | |
|---|---|
| LXXI | 1.30(s,6H); 1.90-2.37(m,1H); 5.12-5.27(m,2H); 6.63-7.00(m,1H); 6.63-7.00(dt,1H); 7.43(s,5H) |
| LXXII | 1.23(s,3H); 1.27(s,3H); 1.75-2.20(m,2H); 5.18-5.25(m,2H); 6.20-6.33(d,1H); 6.63-7.00(dt,1H); 7.43(s,5H) |
| LXXIII | 1.28(s,6H); 1.83-2.37(m,2H); 5.22-5.30(m,2H); 5.70-6.37(q,1H); 6.62-6.98(dt,1H); 7.42(s,5H) |
| LXXV | 1.27-1.52(t,3H); 1.77-2.67(q,2H); 3.83-4.20(q,2H); 5.23(bs,2H); 6.77-7.47(m,11H) |
| LXXVI | 1.23(s,3H); 1.27(s,3H); 1.78-2.00(m,2H); 5.20(bs,2H); 6.68-6.98(m,3H); 7.42(s,5H) |
| LXXVII | 1.23(s,3H); 1.27(s,3H); 1.77-2.23(m,2H); 5.18-5.27(m,2H); 6.20-6.33(d,1H); 6.63-7.00(m,1H); 7.43(s,5H) |
| LXXVIII | 1.23(s,3H); 1.27(s,3H); 1.75-2.12(m,2H); 5.18-5.25(m,2H); 6.63-6.98(m,1H); 6.63-6.98(m,1H); 7.41(s,5H) |
| XCIV | 1.20-1.23(d,3H); 1.39-1.41(d,3H); 1.82-2.10(m,2H); 2.20-2.23(d,3H); 4.97-5.73(m,1H); 5.22-5.27(d,2H); 7.17-7.48(m,8H). |
| XCV | 1.23(s,3H); 1.40(s,3H); 1.85-2.10(m,2H); 2.33(s,3H); 5.23(s,2H); 5.40-5.57(dd,1H); 7.17-7.33(m,8H). |
| XCVI | 1.23(s,3H); 1.43(s,3H); 1.87-2.05(m,2H); 2.27(s,3H); 5.00-5.23(m,1H); 5.30(s,2H); 7.20-7.33(m,8H). |
| XCVII | 1.20-1.23(d,3H); 1.40-1.45(d,3H); 1.70-2.07(m,2H); 2.27-2.37(m,3H); 2.43-2.48(d,3H); 5.10-5.60(m,1H); 5.32-5.37(d,2H); 7.13-7.35(m,7H). |
| XCVIII | 1.20-1.23(d,3H); 1.40-1.43(d,3H); 1.82-2.10(m,2H); 2.20-2.37(m,3H); 5.07-5.57(m,1H); 5.20-5.27(d,2H); 7.26-7.33(m,8H). |
| XCIX | 0.97-1.67(dd,6H); 2.18(s,3H); 3.87-4.13(dd,1H); 5.07-5.25(m,1H); 5.28(s,2H); 6.55-6.70(d,1H); 7.20-7.55(m,8H). |
| C | 1.00-1.15(dd,6H); 2.22(s,3H); 2.43(s,3H); 3.93-4.18(dd,1H); 5.15-5.30(m,1H); 5.47(s,2H); 6.67-6.82(d,1H); 7.27-7.70(m,7H). |

In the normal use of the insecticidal and acaricidal esters of the present invention, the esters usually will not be employed free from admixture or dilution, but ordinarily will be used in a suitable formulated composition compatible with the method of application and comprising an insecticidally or acaricidally effective amount of [1,1'-biphenyl]-3-ylmethyl pyrethroid ester. The esters of this invention, like most pesticidal agents, may be blended with the agriculturally acceptable surface-active agents and carriers normally employed for facilitating the dispersion of active ingredients, recognizing the accepted fact that the formulation and mode of application of an insecticide or acaricide may affect the activity of the material. The present esters may be applied, for example, as sprays, dusts, or granules to the area where pest control is desired, the type of application varying of course with the pest and the environment. Thus, the esters of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the esters. The granule particles are relatively large, a diameter of about 400–2500 microns typically. The particles are either impregnated with the ester from solution or coated with the ester, adhesive sometimes being employed. Granules generally contain 1–15%, preferably 3–10%, active ingredient as the insecticidally effective amount.

Dusts are admixtures of the esters with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects and acarids contains 10 parts of (2,4-difluoro-[1,1'-biphenyl]-3-yl)methyl cis-3-(2,2-dichloroethenyl)-2,2-dimethylcyclopropanecarboxylate, 30 parts of bentonite clay, and 60 parts of talc.

The esters of the present invention may be made into liquid concentrates by dissolution or emulsification in suitable liquids and into solid concentrates by admixture with talc, clays, and other known solid carriers used in the pesticide art. The concentrates are compositions containing, as an insecticidally or acaricidally effective amount, about 5–50% [1,1'-biphenyl]-3-ylmethyl pyrethroid ester, such as (2'-methyl-[1,1'-biphenyl]-3-yl)methyl 3-(2,2-dichloroethenyl)-2,2-dimethylcyclopropanecarboxylate, and 95–50% inert material, which includes surface-active dispersing, emulsifying, and wetting agents. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects and acarids contains 1.5 parts each of sodium lignosulfonate and sodium laurylsulfate as wetting agents, 25 parts of (2'-fluoro-[1,1'-biphenyl]-3-yl)methyl 3-(2,2-dichloroethenyl)-2,2-dimethylcyclopropanecarboxylate, and 72 parts of bentonite clay.

Useful liquid concentrates include the emulsifiable concentrates, which are homogeneous liquid or paste compositions readily dispersed in water or other liquid carriers. They may consist entirely of the ester with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal and acaricidal composition.

Other useful formulations include simple solutions of the active ingredient in a solvent in which it is completely soluble at the desired concentration, such as acetone or other organic solvents.

An insecticidally or acaricidally effective amount of [1,1'-biphenyl]-3-ylmethyl pyrethroid ester in an insecticidal and acaricidal composition diluted for application is normally in the range of about 0.001% to about 2% by weight. Many variations of spraying and dusting compositions known in the art may be used by substituting the esters of this invention into compositions known or apparent to the art.

The insecticidal and acaricidal compositions of this invention may be formulated with other active ingredients, including other insecticides, nematicides, acaricides, fungicides, plant growth regulators, fertilizers, etc. In using the compositions to control insects and acarids, it is only necessary that an insecticidally or acaricidally effective amount of [1,1'-biphenyl]-3-ylmethyl pyrethroid ester be applied to the locus where control is desired, or on or in soil contiguous to the crop to be protected before, during, or after planting said crop. For most applications, an insecticidally or acaricidally effective amount of [1,1'-biphenyl]-3-ylmethyl pyrethroid ester will be about 75 to 4000 g per hectare, preferably 150 g to 3000 g per hectare.

The insecticidal and acaricidal activity of [1,1'-biphenyl]-3-ylmethyl pyrethroid esters of Table 1 were evaluated by application to the locus where control is desired as follows:

The ester (0.25 g) was dissolved in 20 ml of acetone, and this solution was dispersed in 180 ml of water containing one drop of isooctyl phenyl polyethoxyethanol. Aliquots of this solution, containing 1250 ppm ester, were diluted with appropriate amounts of water to provide test solutions containing lesser amounts of the active ingredient.

Test organisms and techniques were as follows: Activities against the Mexican bean beetle (*Epilachna varivestis* Muls.) and the southern armyworm (*Spodoptera eridania* [Cram.]) were evaluated by dipping the leaves of pinto bean plants into the test solution and, when the foliage had dried, infesting the leaves with the appropriate immature insects; activity against the pea aphid (*Acyrthosiphon pisum* [Harris]) was evaluated on broad bean plants whose leaves were dipped before infestation with adult aphids; activity against twospotted spider mites (*Tetranychus urticae* Koch) was evaluated on pinto bean plants whose leaves were dipped after infestation with adult mites; activities against the milkweed bug (*Oncopeltus fasciatus* [Dallas]) and the plum curculio (*Conotrachelus nenuphar* [Herbst]) were evaluated by spraying the test solutions into glass dishes or jars containing the adult insects. All organisms in the tests were maintained in a holding room at 80° F. and 50% relative humidity for an exposure period of 48 hours. At the end of this time, the dead and living insects or mites were counted, and the percent kill was calculated. Results of these tests are summarized in Table 3.

A number of the insecticidal and acaricidal compounds of this invention were also evaluated for efficacy in topical application to various insect species using techniques well known by those skilled in the art. For instance, the compound of Example XXXVII was so evaluated against southern armyworm larvae and other species; $LD_{50}=25$ nanograms/insect was determined from the southern armyworm data.

[1,1'-Biphenyl]-3-ylmethyl pyrethroid esters were evaluated for systemic insecticidal activity as follows: Broad bean (*Vicia faba* var. Windsor) and pinto bean (*Phaseolus vulgaris*) seedlings that had reached a height of 5–6 cm were transplanted from germination flats into a soil of three parts sand and one part peat moss contained in 7.6 cm plastic pots. The transplanted plants were allowed a two-day recovery period to insure that the candidate insecticide did not enter the plants via damaged roots. Before application of the candidate insecticide the soil of the test plants was moistened, but not saturated. The pots of the test plants were placed in a 9.5 cm petrie plate lid, and 25 ml portions of a solution containing 146 ppm (wt/v-8 kg/ha) of the candidate insecticide was poured evenly over the soil surface of each of the test plants, being careful not to wet the foliage or stems. The 146 ppm solution of the candidate insecticide was prepared by dissolving 37 mg of the candidate insecticide in 250 ml of a stock solution of 10% acetone-water, containing one drop of octylphenoxypolyethoxy ethanol per 100 ml of stock solution. The candidate insecticide was allowed a three day translocation period, after which time the plants were infested with the appropriate insects.

Two broad bean plants per rate of application of candidate insecticide were each placed in 1400 ml paper cups. Each replicate was infested with ten pea aphids (*Acyrthosiphon pisum* [Harris]) and covered with a plastic lid. A two day feeding period was observed, after which time the tests were evaluated for insect mortality. Two leaves from each of two pinto bean plants per rate of application of candidate insecticide were removed and placed in two 240 ml paper cups. Each cup was infested with ten of either southern armyworm (*Spodoptera eridania* [Cram.]), Mexican bean beetle (*Epilachna varivestis* Muls.) or cabbage looper (*Trichoplusia ni* [Hubner]), then covered with a plastic lid. A two day feeding period was observed, after which time the tests were evaluated for mortality. Further evaluations of systemic insecticidal activity were done in the manner described above, varying the rate of application of the candidate insecticide. Results of these tests are summarized in Table 4.

TABLE 3

ACTIVITY OF [1,1'-BIPHENYL]-3-YLMETHYL PYRETHROID ESTERS

| COMPOUND OF EX. | Conc. ppm. | Mexican Bean Beetle | Southern Armyworm | Pea Aphid | Twospotted Spider Mite | Milkweed Bug | Plum Curculio |
|---|---|---|---|---|---|---|---|
| I | 1250 | 100 | 100 | 100 | 95.7 | 100 | 100 |
| II | 1250 | 100 | 100 | 100 | 96.6 | 100 | |
| III | 1250 | 100 | 100 | 100 | 0 | 100 | |
| IV | 1250 | 100 | 100 | 100 | 21 | 95.4 | 29 |
| V | 1250 | 100 | 100 | 100 | 61 | 100 | |
| VI | 1250 | 100 | 100 | 100 | 96 | 100 | |
| VII | 1250 | 100 | 100 | 100 | 8 | 100 | |
| VIII | 1250 | 100 | 100 | 100 | 0 | 100 | 100 |
| IX | 1250 | 100 | 100 | 100 | 76 | 50 | 0 |
| X | 1250 | 100 | 100 | 100 | 0 | 100 | 15 |
| XI | 1250 | 100 | 100 | 100 | 100 | 100 | |
| XII | 1250 | 100 | 100 | 100 | 100 | 100 | |
| XIII | 1250 | 100 | 100 | 100 | 100 | 100 | |
| XIV | 1250 | 100 | 100 | 100 | 100 | 100 | 100 |
| XV | 1250 | 100 | 100 | 100 | 0 | 95 | 65 |
| XVI | 1250 | 11 | 100 | 100 | 0 | 99 | |
| XVII | 1250 | 100 | 100 | 90 | 0 | 15 | |
| XVIII | 1250 | 100 | 100 | 100 | 0 | 57 | |
| XIX | 512 | 100 | 100 | 100 | 0 | | |
| XX | 1250 | 94 | 100 | 100 | 0 | 91 | 30 |
| XXIII | 512 | 100 | 100 | 100[a] | 94[a] | | |
| XXIV | 1250 | 100 | 100 | 100 | 96.1 | 100 | |
| XXVII | 1250 | 100 | 100 | 100 | 78 | 100 | |
| XXX | 1250 | 100 | 100 | 100 | 74 | 100 | 100 |
| XXXIII | 1250 | 71 | 100 | 100 | 0 | 100 | |
| XXXIV | 1250 | 100 | 100 | 100 | 100 | 100 | |
| XXXVI | 512 | 100 | 100 | 89 | 0 | | |
| XXXVII | 64 | 100 | 100 | 100 | 100 | | |
| XXXVIII | 64 | 90 | 100 | 40 | 100 | | |
| XXXIX | 64 | 100 | 100 | 100 | | | |
| XL | 64 | 100 | 100 | 100 | 0 | | |
| XLI | 64 | 100 | 100 | 100 | 0 | | |
| XLII | 64 | 100 | 100 | 100 | 0 | | |
| XLIII | 64 | 0 | 100 | 70 | | | |
| XLIV | 64 | 100 | 100 | 100 | 100 | | |
| XLV | 64 | 95 | 100 | 100 | 52 | | |
| XLVI | 64 | 100 | 100 | 95 | 75 | | |
| XLVII | 64 | 70 | 100 | 100 | 0 | | |
| XLVIII | 64 | 45 | 55 | 5 | | | |
| XLIX | 64 | 100 | 100 | 90 | 100 | | |
| L | 64 | | 100 | | 0 | | |
| LI | 500 | | 100 | 100 | 0 | | |
| LII | 500 | | 100 | 100 | 0 | | |
| LIII | 500 | | 100 | 100 | 0 | | |
| LIV | 500 | | 100 | 100 | 0 | | |
| LV | 500 | | 100 | 90 | 0 | | |
| LVI | 312 | 63 | 100 | 72 | | | |
| LVII | 500 | | 100 | 70 | 0 | | |
| LVIII | 312 | 100 | 85 | 93 | 0 | | |
| LIX | 312 | 50 | 100 | 25 | | | |
| LX | 64 | | 95 | 30 | | | |
| LXI | 64 | 75 | 100 | 60 | 0 | | |
| LXII | 64 | 85 | 60 | 100 | | | |
| LXI | 64 | 100 | 100 | 0 | | | |
| LXIV | 64 | 100 | 25 | 100 | | | |
| LXX | 16 | 100 | 100 | 100 | 12 | | |
| LXXI | 500 | | 100 | 100 | 100 | | |
| LXXIII | 500 | | 100 | 100 | 100 | | |
| LXXIV | 64 | 100 | 100 | 100 | 0 | | |
| LXXXVI | 500 | | 100 | 95 | 0 | | |
| LXXXVII | 500 | | 100 | 85 | 0 | | |
| LXXXVIII | 500 | | 100 | 65 | 0 | | |
| LXXXIX | 500 | | 100 | 100 | 0 | | |
| XC | 500 | | 100 | 100 | 0 | | |
| XCI | 500 | | 100 | 70 | 0 | | |
| XCII | 500 | | 100 | 100 | 0 | | |
| XCIII | 500 | | 100 | 50 | 0 | | |
| XCIV | 500 | | 100 | 100 | 100 | | |
| XCV | 500 | | 100 | 70 | 60 | | |
| XCVI | 500 | | 100 | 100 | 100 | | |
| XCVII | 500 | | 100 | 100 | 0 | | |
| XCVIII | 500 | | 100 | 100 | 0 | | |
| XCIX | 64 | 100 | | 40 | 66 | | |
| C | 1250 | | 95 | 100 | 100 | | |

[a]500 ppm

TABLE 4

SYSTEMIC ACTIVITY OF [1,1'-BIPHENYL]-3-YLMETHYL PYRETHROID ESTERS

| COMPOUND OF EX. | Conc. ppm. | Percent Kill | | | |
|---|---|---|---|---|---|
| | | Pea Aphid | Mexican Bean Beetle | Southern Armyworm | Cabbage Looper |
| XL | 146 | 100 | 0 | 0 | |
| XLI | 146 | 95 | 0 | 0 | |
| | 2000 | | 35 | | 50 |
| LXX | 500 | 100 | 50 | | 94 |
| | 146 | 100 | 0 | 0 | |
| LXXI | 2000 | | 35 | 0 | |
| | 1000 | 80 | 10 | | |
| LXXII | 2000 | | 40 | 50 | |
| | 1000 | 35 | | 50 | |
| LXXIII | 2000 | | 0 | 50 | |
| | 1000 | 60 | | 50 | |
| LXXIV | 146 | 15 | 0 | 80 | |
| | 500 | | | | 0 |
| LXXV | 146 | 65 | 0 | 0 | |
| LXXVI | 146 | 90 | 5 | 0 | |
| LXXVII | 146 | 90 | 45 | 0 | |
| LXXVIII | 146 | 100 | 100 | 0 | |
| LXXIX | 2000 | | 25 | 0 | |
| | 1000 | 0 | 15 | | |
| LXXX | 146 | 100 | 0 | 0 | |
| LXXXI | 146 | 30 | 0 | 0 | |
| LXXXII | 146 | 50 | 0 | 0 | |
| LXXXIII | 146 | 0 | 5 | 0 | |
| LXXXIV | 146 | 10 | 0 | 0 | |
| LXXXV | 146 | 85 | 0 | 0 | |

I claim:

1. A compound of the formula

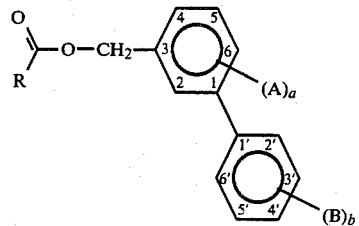

wherein (1) b is 0, a is 3 or 4, and R is selected from 2,2,3,3-tetramethylcyclopropyl, 2,2-dichloro-3,3-dimethylcyclopropyl, 3-cyclopentylidenemethyl-2,2-dimethylcyclopropyl, 3-(2-methyl-1-propenyl)-2,2-dimethylcyclopropyl, and 3-(1,2-dibromo-2,2-dichloroethyl)-2,2-dimethylcyclopropyl, and when a is 3, A is fluoro, or A is 2-chloro, 2-bromo, 2-methyl, or 2-ethyl with two additional fluoro groups, or A is 2- and 4-substituents independently selected from fluoro, chloro and methyl with one additional fluoro group, and when a is 4, A is fluoro, or A is 2- and 4-substituents independently selected from fluoro, chloro and methyl with two additional fluoro groups; or R is selected from 3-[(2-chloro-2-phenyl)ethenyl]-2,2-dimethylcyclopropyl, 1-(4-chlorophenyl)-2-methylpropyl, 2,2-dichloro-1-(4-ethoxyphenyl)-cyclopropyl, and 1-(2-chloro-4-trifluoromethylphenylamino)-2-methylpropyl, a is 3 or 4, and A is fluoro; or (2) a is 3 or 4, b is 4, R is selected from 3-(2,2-dichloroethenyl)-2,2-dimethylcyclopropyl and 3-(2,2-dibromoethenyl)-2,2-dimethylcyclopropyl, and A is fluoro or a 2-substituent selected from chloro, bromo, and lower alkyl with 2 or 3 fluoro groups, and B is fluoro or a 2'-substituent selected from chloro and methyl with 3 fluoro groups.

2. An insecticidal or acaricidal composition comprising an insecticidally or acaricidally effective amount of at least one compound of claim 1 in admixture with an agriculturally acceptable carrier.

3. A method of controlling insects or acarids which comprises applying to the locus where control is desired an insecticidally or acaricidally effective amount of at least one compound of claim 1.

* * * * *